(12) United States Patent
Hershko et al.

(10) Patent No.: US 10,933,022 B2
(45) Date of Patent: *Mar. 2, 2021

(54) PROTEASE INHIBITOR-CONTAINING COMPOSITIONS, COMPOSITIONS COMPRISING SAME, AND METHODS FOR PRODUCING AND USING SAME

(71) Applicant: Oramed Ltd., Jerusalem (IL)

(72) Inventors: Avraham Hershko, Haifa (IL); Miriam Kidron, Jerusalem (IL)

(73) Assignee: Oramed Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/407,737

(22) Filed: May 9, 2019

(65) Prior Publication Data

US 2019/0321303 A1 Oct. 24, 2019

Related U.S. Application Data

(63) Continuation of application No. 14/376,292, filed as application No. PCT/IL2013/050091 on Jan. 31, 2013, now Pat. No. 10,342,764.

(60) Provisional application No. 61/634,753, filed on Mar. 6, 2012, provisional application No. 61/632,868, filed on Feb. 1, 2012.

(51) Int. Cl.
| | |
|---|---|
| *C07K 14/81* | (2006.01) |
| *A61K 9/48* | (2006.01) |
| *A61K 9/19* | (2006.01) |
| *A61K 38/17* | (2006.01) |
| *A61K 38/26* | (2006.01) |
| *A61K 38/28* | (2006.01) |
| *A61K 47/42* | (2017.01) |
| *A61K 38/56* | (2006.01) |

(52) U.S. Cl.
CPC .............. *A61K 9/4866* (2013.01); *A61K 9/19* (2013.01); *A61K 9/4858* (2013.01); *A61K 9/4875* (2013.01); *A61K 9/4891* (2013.01); *A61K 38/17* (2013.01); *A61K 38/26* (2013.01); *A61K 38/28* (2013.01); *A61K 38/56* (2013.01); *A61K 47/42* (2013.01)

(58) Field of Classification Search
CPC .............................. C07K 14/811; C07K 14/81
See application file for complete search history.

(56) References Cited

U.S. PATENT DOCUMENTS

| | | |
|---|---|---|
| 4,579,730 A | 4/1986 | Kidron et al. |
| 5,034,415 A | 7/1991 | Rubin |
| 5,206,219 A | 4/1993 | Desai |
| 5,665,700 A | 9/1997 | Cho et al. |
| 5,824,638 A | 10/1998 | Burnside et al. |
| 6,692,766 B1 | 2/2004 | Rubinstein et al. |
| 6,761,903 B2 | 7/2004 | Chen et al. |
| 6,858,576 B1 | 2/2005 | Young et al. |
| 7,404,973 B2 | 7/2008 | Konwinski et al. |
| 9,186,412 B2 | 11/2015 | Kidron et al. |
| 9,259,456 B2 | 2/2016 | Kidron |
| 10,010,503 B2 | 7/2018 | Kidron et al. |
| 10,058,593 B2 | 8/2018 | Kidron |
| 10,342,764 B2 | 7/2019 | Hershko et al. |
| 10,350,162 B2 | 7/2019 | Kidron |
| 10,398,762 B2 | 9/2019 | Kidron |
| 10,420,721 B2 | 9/2019 | Kidron et al. |
| 2002/0032171 A1 | 3/2002 | Chen et al. |
| 2003/0118610 A1 | 6/2003 | Stern et al. |
| 2004/0097410 A1 | 5/2004 | Zheng et al. |
| 2005/0143303 A1 | 6/2005 | Quay et al. |
| 2005/0232981 A1 | 10/2005 | Ben-Sasson |
| 2006/0018874 A1 | 1/2006 | Radhakrishnan et al. |
| 2006/0045868 A1 | 3/2006 | Meezan et al. |
| 2006/0045869 A1 | 3/2006 | Meezan et al. |
| 2006/0234913 A1 | 10/2006 | Arbit et al. |
| 2006/0264401 A1 | 11/2006 | Campbell et al. |
| 2006/0286129 A1 | 12/2006 | Sarubbi |
| 2006/0293232 A1 | 12/2006 | Levy et al. |
| 2007/0077283 A1 | 4/2007 | Quay et al. |
| 2007/0086972 A1 | 4/2007 | Birnbaum |
| 2007/0087957 A1 | 4/2007 | Kidron |
| 2011/0014247 A1 | 1/2011 | Kidron |
| 2011/0046053 A1 | 2/2011 | Kidron |
| 2011/0166062 A1 | 7/2011 | DiMarchi et al. |
| 2013/0195939 A1 | 8/2013 | Kidron |
| 2014/0377344 A1 | 12/2014 | Hershko et al. |
| 2015/0017238 A1 | 1/2015 | Kidron |
| 2015/0335715 A1 | 11/2015 | Kidron et al. |
| 2016/0206703 A1 | 7/2016 | Kidron |

(Continued)

FOREIGN PATENT DOCUMENTS

| | | |
|---|---|---|
| CA | 1223200 A1 | 6/1987 |
| CA | 2621577 A1 | 3/2007 |

(Continued)

OTHER PUBLICATIONS

Yu, Y-H et al., "Recent progress on the study of soybean Bowman-Birk trypsin inhibitor," Chin J. Dis Control Prey 9(2):150-153 (Apr. 2005), Chinese Preventive Medicine Association, China.

(Continued)

*Primary Examiner* — Karen Cochrane Carlson

(74) *Attorney, Agent, or Firm* — Sterne, Kessler, Goldstein & Fox P.L.L.C.

(57) ABSTRACT

Provided herein are methods and compositions for oral administration of therapeutic proteins, improved protease inhibitor preparations, methods for producing same, and compositions comprising same.

26 Claims, 15 Drawing Sheets

Specification includes a Sequence Listing.

(56) References Cited

U.S. PATENT DOCUMENTS

| | | |
|---|---|---|
| 2018/0369339 A1 | 12/2018 | Kidron |
| 2019/0209655 A1 | 7/2019 | Kidron et al. |

FOREIGN PATENT DOCUMENTS

| | | |
|---|---|---|
| CN | 101095942 A | 2/2008 |
| CN | 101242748 A | 8/2008 |
| CN | 102037121 A | 4/2011 |
| EP | 0351651 A2 | 1/1990 |
| IL | 68769 A | 2/1986 |
| JP | 02-250823 | 10/1990 |
| JP | 09/208485 A | 8/1997 |
| JP | 10-330287 A | 12/1998 |
| JP | 00/050793 A | 2/2000 |
| JP | 2001/240558 A | 9/2001 |
| JP | 2005-525308 | 8/2005 |
| JP | 2011-515458 | 5/2011 |
| KR | 01/0069433 A | 7/2001 |
| KR | 2001/0069322 A | 7/2001 |
| RU | 2104715 C1 | 2/1998 |
| WO | WO 91/14454 A1 | 10/1991 |
| WO | WO 97/03688 | 2/1997 |
| WO | WO 00/24424 A1 | 7/2000 |
| WO | WO 2003/057170 A2 | 7/2003 |
| WO | WO 2006/057551 A1 | 6/2006 |
| WO | WO 2009/118722 A2 | 10/2009 |
| WO | WO 2011/082335 A2 | 7/2011 |
| WO | WO 2011/082338 A1 | 7/2011 |
| WO | WO 2013/102899 A1 | 7/2013 |
| WO | WO 2019/239405 A1 | 12/2019 |

OTHER PUBLICATIONS

Yang, Z et al., "Progress in Soybean Trypsin Inhibitor," Feed Review, Issue 12, pp. 31-33 (Dec. 2005), Si Liao Bo Lan Bian Ji Bu publisher, China.

[No Author listed] Sigma-Aldrich, Feb. 2017. T9128. Trypsin inhibitor from Glycine max (soybean). At www.sigmaaldrich.com/catalog/product/sigma/t9128?lang+en®ion=US downloaded Feb, 27, 2017.

Kunitz et al., Crystalline soybean trypsin inhibitor: II. General Properties. J. Gen. Physiol. Mar. 20, 1947:30(4):291-310.

Morishita et al., Novel oral microspheres of insulin with protease inhibitor protecting from enzymatic degradation. Int J. Pharm. 78 (1992) 1-7.

Nadeau et al., Treatment of non-alcoholic fatty liver disease with metformin versus lifestyle intervention in insulin-resistant adolescents. Pediatr. Diabetes. Feb. 2009:10(1):5-13. Doi: 10.1111/j. 1399-5448. 2008.00450.x. Epub Aug. 20, 2008.

Park et al., Oral protein delivery: Current status and future prospect. Reactive and Functional Polymers. 71 (Mar. 2011) 280-287.

Shyangidan et al., Insulin sensitisers in the treatment of non-alcoholic fatty liver disease: a systematic review. Health Technol Assess. Nov. 2011; 15(38):1-110. doi: 10.3310/hta 15380.

International Search Report and Written Opinion for International Application No. PCT/IL2013/050091 dated May 9, 2013.

International Preliminary Report on Patentability for International Application No. PCT/IL2013/050091 dated Aug. 14, 2014.

[No Author Listed] Cure Talk (retrieved from http://trialx.com/curetalk/2012/05/type-2-diabetes-difficult-to-treat-in-children-new-study/ on Apr. 22, 2015, 2 pages).

[No Author Listed] Joslin Diabetes Center (retrieved from http://www.joslin.org/info/will diabetes go away.html on Apr. 22, 2015, 2 pages).

[No Author Listed] The Observer (retrieved from http://observer.com/2014/02/tough-to-swallow-paper-trail-breakthrough-leads-to-penny-stock-profiteers/ on Apr. 22, 2015, 5 pages).

[No Author Listed] WebMD (retrieved from http://www.webmd.com/diabetes/is-there-a-diabetes-cure on Apr. 22, 2015, 3 pages).

Agarwal, et al.; "Oral Delivery of Proteins: Effect of Chicken and Duck Ovomucoid on the Stability of Insulin in the Presence of a-Chymotrypsin and Trypsin"; Pharm. Pharmacal. Commun.; (May 2000); 6: 223-227.

Bar-On et al., Enteral administration of insulin in the rat. Br J Pharmacal. May 1981;73(1):21-4.

Bendayan, et al.; "Biochemical and morpho-cytochemical evidence for the intestinal absorption of insulin in control and diabetic rats. Comparison between the effectiveness of duodenal and colon mucosa"; Diabetologia (Feb. 1994); 37: 119-126.

Bendayan, et al.; "Morpho-cytochemical and biochemical evidence for insulin absorption by the rat ileal epithelium"; Diabetologia (Apr. 1990); 33: 197-204.

Birk, Trypsin and chymotrypsin inhibitors from soybeans. Methods Enzymol. 1976;45:700-7.

Carino, et al.; "Oral insulin delivery"; Advanced Drug Delivery Review (Feb. 1999); 35: 249-257.

Cernea, et al.; "Comparison of pharmacokinetic and pharmacodynamic properties of single-dose oral insulin spray and subcutaneous insulin injection in healthy subjects using the euglycemic clamp technique"; Clinical Therapeutics (Dec. 2004); 26(12): 2084-2091.

Cernea, et al.; "Dose-Response Relationship of an Oral Insulin Spray in Six Patients with Type 1 Diabetes: A Single-Center, Randomized, Single-Blind, 5-Way Crossover Study"; Clinical Therapeutics (Oct. 2005); 27(10): 1562-1570.

Cernea, et al.; "Dose-Response Relationship of Oral Insulin Spray in Healthy Subjects"; Diabetes Care (Jun. 2005); 28(6): 1353-1357.

Chiquette, et al., Treatment with exenatide once weekly or twice daily for 30 weeks is associated with changes in several cardiovascular risk markers. Vase Health Risk Manag. 2012;8:621-9. doi: 10.2147NHRM.S37969. Epub Nov. 12, 2012.

Cole, et al.; "Challenges and opportunities in the encapsulation of liquid and semi-solid formulations into capsules for oral administration"; Advanced Drug Delivery Reviews (Mar. 2008); 60:747-756.

Cournarie, et al.; "Insulin-loaded W/O/W multiple emulsions: comparison of the performances of systems prepared with medium-chain-triglycerides and fish oil"; Euro. J. of Pharmaceutics and BioPharmaceutics; (Nov. 2004); 58(3): 477-482.

Eldor, et al., A Single-Blind, Two-Period Study to Assess the Safety and Pharmacodynamics of an Orally Delivered GLP-1 Analog (Exenatide) in Healthy Subjects American Diabetes Association 70th Annual Scientific Sessions, Jun. 25-29, 2010A, Orlando, Florida.

Eldor et al., Open-label study to assess the safety and pharmacodynamics of five oral insulin formulations in healthy subjects.Diabetes Obes Metab. Mar. 2010;12(3):219-23. doi:10.1111/j.1463-1326. 2009.01153.x.

Eldor et al., Novel glucagon-like peptide-1 analog delivered orally reduces postprandial glucose excursions in porcine and canine models. J Diabetes Sci Technol. Nov. 1, 2010; 4(6):1516-23.

Gershanik et al., Self-dispersing lipid formulations for improving oral absorption of lipophilic drugs. European Journal of Pharmaceuticals and Biopharmaceutics. (Jul. 2000); 50:179-188.

Gowthamarajan & Kulkarni; Oral Insulin—Fact or Fiction—Possibilities of Achieving Oral Delivery for Insulin; Resonance (May 2003); 8:38-46.

Griffin, Calculation of HLB Values of Non-Ionic Surfactants. J Soc Cosmetic Chemists 5:249 (Jan. 1954).

Hays, et al.; "Prevention and Treatment of Type 2 Diabetes: Current Role of Lifestyle, Natural Product, and Pharmacological Interventions"; Pharmacal. Ther. (2008); 118(2): May 181-191.

Heine, et al.; "Exenatide versus Insulin Glargine in Patients with Suboptimally Controlled Type 2 Diabetes"; American College of Physicians—Annals of Internal Medicine (Oct. 2005); 143(8): 559-569.

Iyer, et al.; "Oral insulin—a review of current status"; Diabetes, Obesity and Metabolism (Mar. 2010); 12: 179-185.

Kidron, et al.; "A novel per-oral insulin formulation: proof of concept study in non-diabetic subjects"; Diabetic Medicine (Apr. 2004); 21: 354-357.

(56) References Cited

OTHER PUBLICATIONS

Kidron, et al.; "Extended exposure to an oral insulin formulation yields decreased insulin secretion in Type II diabetes subjects"; Diabetes Technology Meeting Nov. 11-13, 2010.
Koide et al., The amino acid sequence of soybean trypsin inhibitor. J. Biochem. (Jan. 1972); 71:165-7.
Lasserson, et al.; "Optimal insulin regimens in type 2 diabetes mellitus: systematic review and meta-analyses"; Diabetologia (Oct. 2009); 52: 1990-2000.
Li and Deng; "Oil-based formulation for oral delivery of insulin"; J. Pharmacy Pharmacol (Sep. 2004); 56:1101-1107.
Ma, et al.; "In vitro and in vivo evaluation of a novel oral insulin formulation"; Acta Pharmacologica Sinica (Oct. 2006); 27(10): 1382-1388.
Mack, et al.; "Antiobestiy action of peripheral exenatide (exendin-4) in rodents: effects on food intake, body weight, metabolic status and side-effect measures"; International Journal of Obesity (Sep. 2006); 30: 1332-1340.
Maher, S. et al.; "Safety and efficacy of sodium caprate in promoting oral drug absorption: from in vitro to the clinic"; Advanced Drug Delivery Reviews; (Dec. 2009); 61: 1427-1449.
Martinez-Colubi et al., Switching to darunavir/ritonavir monotherapy (DRV/r mx): effect on kidney function and lipid profile. J Int AIDS Soc. Nov. 11, 2012;15(6):18348. doi:10.7448/IAS.15.6.18348.
Miyagawa, Jun-ichiro; Med Sci Digest (Apr. 2008) 34(4):147-150.
Miyashita et al., Hepatoprotective effect of tamoxifen on steatosis and non-alcoholic steatohepatitis in mouse models. J Toxicol Sci. (Oct. 2012); 37(5):931-42.
Morishita, et al.; "Hypoglycemic effect of novel oral microspheres of insulin with protease inhibitor in normal and diabetic rats"; Int. J. of Pharma; (Dec. 1992); 78: 9-16.
Nissan, et al.; "Intestinal absorption of low molecular weight heparin in animals and human subjects"; Haemostasis (Sep.-Oct. 2000); 30: 225-232.
Onuki, et al.; "In vivo effects of highly purified docosahexaenoic acid on rectal insulin absorption"; Int. J. of Pharmaceutics; (Apr. 2000); 198(2): 147-156.
Ozawa et al., The reactive site of trypsin inhibitors.] Biol Chern. Sep. 10, 1966;241(17):3955-61.
Ray Dirks Research; "Novo Nordisk Sitting on $2 Billion in Cash May Look to Acquire Oramed or ISIS for Oral Insulin"; May 31, 2012.
Raz, et al.; "Rectal Administration of Insulin"; Israel Journal of Medical Sciences (Feb. 1984); 20:173-175.
Ryan et al., Assessment of the severity of hypoglycemia and glycemic lability in type 1 diabetic subjects undergoing islet transplantation. Diabetes. Apr. 2004;53(4):955-62.
Sherman, "Oramed Enrolls First Patient in its Phase 2a U.S. Oral Insulin Clinical Trial"; Jul. 8, 2013.
Siepmann et al., Blends of aqueous polymer dispersions used for pellet coating: importance of the particle size. J Control Release. Jul. 20, 2005; 105(3):226-39.
Silva-Cunha et al.; "W/O/W multiple emulsions of insulin containing a protease inhibitor and an absorption enhancer: preparation, characterization and determination of stability towards proteases in vitro"; Int. J. of Pharmaceutics; (Dec. 1997); 158(1): 79-89.
Sprecher et al., Molecular cloning, expression, and partial characterization of two novel members of the ovalbumin family of serine proteinase inhibitors. J Biol Chern. Dec. 15, 1995;270(50):29854-61.
Sun et al., Gene structure, chromosomal localization, and expression of the murine homologue of human proteinase inhibitor 6 (PI-6) suggests divergence of PI-6 from the ovalbumin serpins. J Biol Chern. Jul. 7, 1995;270(27):16089-96.
Tesauro et al., Effects of GLP-1 on forearm vasodilator function and glucose disposal during hyperinsulinemia in the metabolic syndrome. Diabetes Care. Mar. 2013;36(3):683-9. doi: 10.2337/dc12-0763. Epub Oct. 15, 2012.
Umeza W A, Structures and activities of protease inhibitors of microbial origin. Methods Enzymol. 1976;45:678-95.
Yeboah et al., A rapid purification method for soybean Bowman-Birk protease inhibitor using hydrophobic interaction chromatography. Protein Expression and Purification. (May 1996); 7:309-14.
Ziv, et al.; "Absorption of Protein via the Intestinal Wall A Quantitative Model"; Biochemical Pharmacology (Apr. 1987); 36(7): 1035-1039.
Ziv, et al.; "Bile Salts Promote the Absorption ofInsulin from the Rat Colon"; Life Sciences (Aug. 1981); 29: 803-809.
Ziv, et al.; "Oral administration of insulin in solid form to nondiabetic and diabetic dogs"; Journal of Pharmaceutical Sciences (Jun. 1994); 83(6): 792-794.
Worthington Biochemical Corporation (2016); Trypsin inhibitors C.A.S.: 9035-81-1. On the at worthingon-biochem.com/TI/default. html downloaded Jul. 19, 2016.
Koide, et al., Studies on soybean trypsin inhibitors. 3. Amino acid sequence of the carboxy terminal region and complete amino acid sequence of soybean trypsin inhibitor (Kunutz). Eur. J. Biochem. 32: 417-431 (1973).
Sigma-Aldrich, Feb. 2017. T9128. Trypsin inhibitor from Glycine max (soybean). At www.sigmaaldrich.com/catalog/product/sigma/t9128?lang+en®ion=US, downloaded Feb. 27, 2017.
Kunitz, Crystalline soybean trypsin inhibitor II General Properties J. Gen Physiol. 30(4):291-310 (Mar. 1947).
Doctors Supplements Store. Dec. 2015, on the web at doctors-supplementstore.com/what-makes-a-supplement-pharmaceutical-grade/; pp. 1-2, downloaded Sep. 19, 2017.

Flow Diagram of
SBTI Intermediate

Day 1: Buffer preparations
Extraction buffer: 25 mM sodium phosphate, 100 mM NaCl, pH 4.5.
Dialysis buffer: 10 mM sodium phosphate, pH 6.5

↓

Day 2: Soy flour extraction
Mix 25 Kg flour with 250 L Extraction buffer for 1 hour at RT

↓

Day 2: Clarification
Add 7.5 Kg Hyflo, mix and transfer through filter press. Collect supernatant. Wash the filter press with 80 L Extraction buffer

↓

Day 2: Ammonium Sulfate Precipitation
Combine extraction of 2 x 25 Kg and add Ammonium Sulfate, 0.209 Kg/L (35% saturated). Mix 2 hr in RT. Store overnight < 15°C

↓

Day 3: Collect Ammonium Sulfate Precipitate
Centrifuge by continuous tubular centrifuge ("Sharples") and retain the pellet.

FIG. 1A

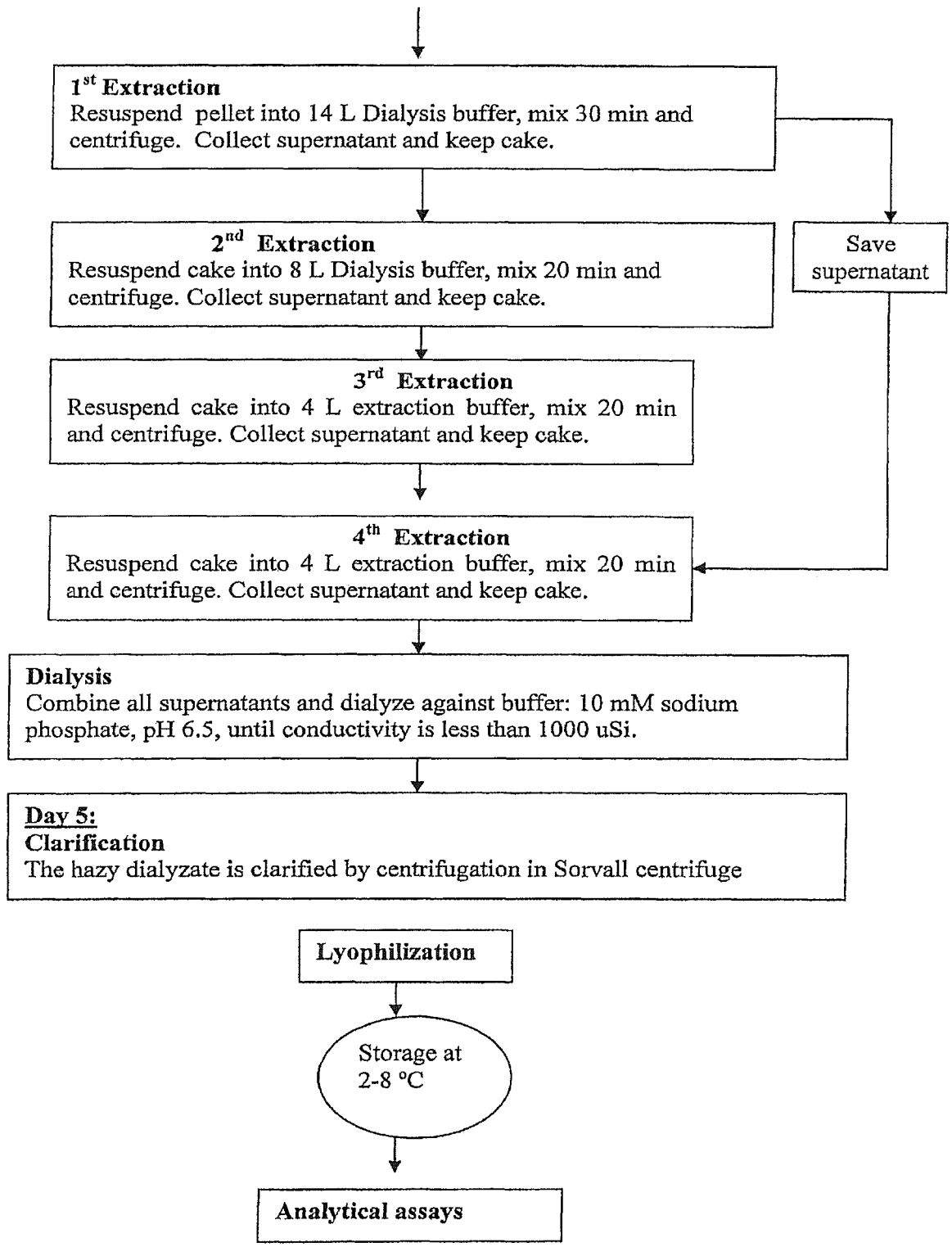
FIG. 1A, continued

ST: Control, T9003, 1mg/ml.
BBI: 1 mgS/ml

| trial sequence | trial no. | Lecithin | GMS | Tween 80 | Gelucire 44/14 | density | foam buildup | test of the suspension in water | sedimentation | decision feasibility | Effectiveness (1=lowest) |
|---|---|---|---|---|---|---|---|---|---|---|---|
| I Lecithin | a | 5% |  |  |  |  | 3 | 1-2 | strong, after 2 hours | aborted 18 hours after preparation due to the sedimentation |  |
|  | b* | 5% | 2% |  |  | 1.0658 | 2 | 2 | not visible | sent for testing | t.b.d. |
|  | c | 10% |  |  |  |  | 4 | n.a. | n.a. | aborted due to foam building |  |
| II Tween 80 | a |  |  | 2% |  |  | 1 | n.a. | strong, after 1 hour | aborted 2 hours after preparation due to the sedimentation |  |
|  | b |  |  | 4% |  |  | 1 | n.a. | strong, after 1 hour | aborted 2 hours after preparation due to the sedimentation |  |
|  | c |  |  | 20% |  |  | 1 | n.a. | strong, after 1 hour | aborted 2 hours after preparation due to the sedimentation |  |
|  | d |  |  | 10% |  |  | 1 | n.a. | strong, after 1 hour | aborted 2 hours after preparation due to the sedimentation |  |
|  | e |  | 2% | 2% |  |  | 1 | 2-3 | moderate, after 1 hour | aborted 18 hours after preparation due to the sedimentation |  |
|  | f |  | 2% | 4% |  |  | 1 | 2-3 | moderate, after 1 hour | aborted 18 hours after preparation due to the sedimentation |  |
|  | g |  | 2% | 20% |  |  | 1 | n.a. | strong, after 1 hour | aborted 2 hours after preparation due to the sedimentation |  |
|  | h |  | 2% | 10% |  |  | 1 | 3 | moderate, after 1 hour | aborted 18 hours after preparation due to the sedimentation |  |

FIG. 11

| | | | | | | | | |
|---|---|---|---|---|---|---|---|---|
| a | | | | | | | | aborted immediately after preparation due to low viscosity |
| b | | | 2% | | 1 | n.a. | n.a. | aborted after 18 hours due to lower viscosity than IIIj |
| c | | | 4% | | 1 | 1-2 | stable after 18 hours | aborted after 18 hours due to lower viscosity than IIIj |
| d* | 3 | | 8% | | 1 | 2 | stable after 18 hours | |
| e* | 6 | | 12% | 1.0443 | 1 | 1-2 | a very thin oil layer (1mm) visible after 18 hours | sent for testing 2 |
| g* | | 5 | 12% | 1.0565 | 1 | 1-2 | a very thin oil layer (1mm) visible after 18 hours | sent for testing |
| h* | | 10 | 12% | 1.0604 | 1 | 2-3 | a very thin oil layer (1mm) visible after 18 hours | sent for testing 4 |
| j* | | | 12% | 1.0599 | 1 | 2-3 | a very thin oil layer (1mm) visible after 18 hours | sent for testing 4 |
| III Gelucire 44/14 | | | 12% | 1.0644 | 1 | 3.5 | stable after 18 hours | sent for testing 2 |

Continuation of FIG. 11

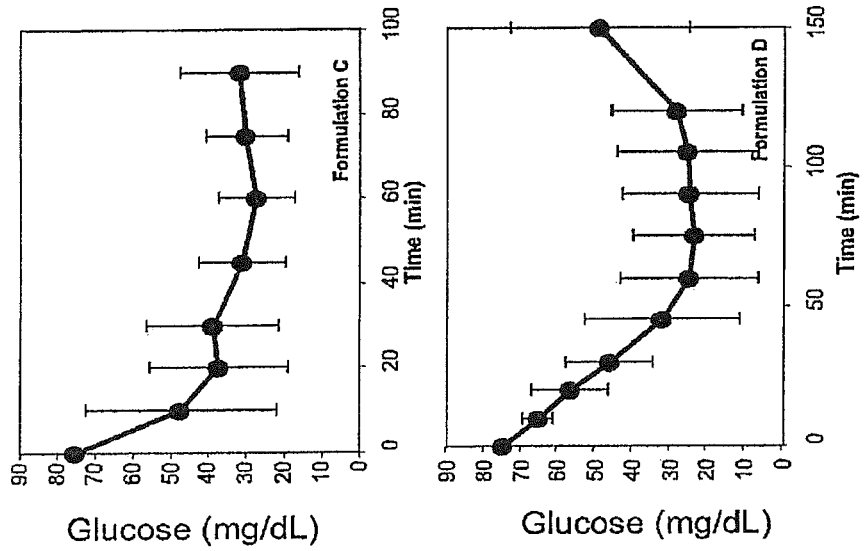
FIG. 12A-3
FIG. 12A-4
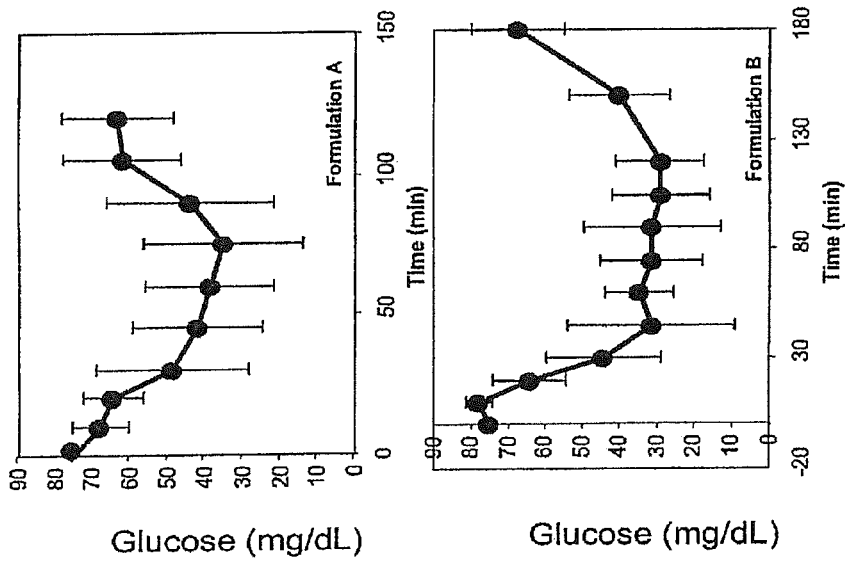
FIG. 12A-1
FIG. 12A-2

FIG. 13A  Blood Sugar Record - Name ____    If glucose under 3.0 mmol, record details on reverse. Date: ____

| Time | 0100 | 0200 | 0300 | 0400 | 0500 | 0600 | 0700 | 0800 | 0900 | 1000 | 1100 | 1200 | 1300 | 1400 | 1500 | 1600 | 1700 | 1800 | 1900 | 2000 | 2100 | 2200 | 2300 | 2400 |
|---|---|---|---|---|---|---|---|---|---|---|---|---|---|---|---|---|---|---|---|---|---|---|---|---|
| Blood Sugar | | | | | | | | | | | | | | | | | | | | | | | | |
| Insulin Taken | | | | | | | | | | | | | | | | | | | | | | | | |

FIG. 13B   For Every Reading Below 3.0 mmol, Please Record Details On Hypoglycemia Sheet Date: ____    Time: ____    Blood sugar Value: ____

Sweating    Problems with vision  Other ____

Shaking    Change in behavior

Heart palpitations   Confusion

The reaction was recognized by (Please circle one):

Yourself    Routine test on your meter    OR    Someone else    None

Treatment for the reaction needed (Please circle all that apply):

Juice/Food    Help from someone else    Injection of Glucagon    Hospital/Ambulance The daily panel shown (A) is repeated seven times so that a week's records is on one page. On the reverse of each sheet (B), a questionnaire is provided for details of each hypoglycemia episode (glucose < 3.0 mmol/l); this is repeated four times for each page.

Scoring Sheet for Hypoglycemia

Episodes of hypoglycemia associated with reduced awareness    Date:

| | | Glucose 2.5 – 2.9Mm | | OR | Glucose < 2.5mM | | |
|---|---|---|---|---|---|---|---|
| | | Max Score | Episode | Max Score | Episode | Per 4 Wks | Per YR |
| Occurrence | | 1 | | 2 | | | |
| Symptoms | Autonomic | 0 | | 0 | | | |
| If no autonomic symptoms, choose highest | Visual | 1 | | 2 | | | |
| | Behavioural | 1 | | 2 | | | |
| | Other Neuro | 1 | | 2 | | | |
| | Confusion | 2 | | 4 | | | |
| | None | 4 | | 8 | | | |
| | Seizures | 6 | | 12 | | | |
| Outside help to (choose highest) | Recognize | 6 | | 12 | | | |
| | Treat | 10 | | 20 | | | |
| | Subtotal | | | | | | |
| By history in last year (per episode) | Outside help to recognize | | 6 | | | | |
| | Outside help to treat | | 10 | | | | |
| | Glucagon | | 40 | | | | |
| | Ambulance | | 80 | | | | |
| TOTAL HYPOGLYCEMIA SCORE | | | | | | | |

FIG. 14

```
SEQUENCE LISTING

<160> NUMBER OF SEQ ID NOS: 5

<210> SEQ ID NO 1
<211> LENGTH: 39
<212> TYPE: PRT
<213> ORGANISM: Glycine max

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 216
<212> TYPE: PRT
<213> ORGANISM: Glycine max

<400> SEQUENCE: 2

Met Lys Ser Thr Ile Phe Phe Leu Phe Leu Phe Cys Ala Phe Thr Thr
1               5                   10                  15

Ser Tyr Leu Pro Ser Ala Ile Ala Asp Phe Val Leu Asp Asn Glu Gly
            20                  25                  30

Asn Pro Leu Glu Asn Gly Gly Thr Tyr Tyr Ile Leu Ser Asp Ile Thr
        35                  40                  45

Ala Phe Gly Gly Ile Arg Ala Ala Pro Thr Gly Asn Glu Arg Cys Pro
    50                  55                  60

Leu Thr Val Val Gln Ser Arg Asn Glu Leu Asp Lys Gly Ile Gly Thr
65                  70                  75                  80

Ile Ile Ser Ser Pro Tyr Arg Ile Arg Phe Ile Ala Glu Gly His Pro
                85                  90                  95

Leu Ser Leu Lys Phe Asp Ser Phe Ala Val Ile Met Leu Cys Val Gly
            100                 105                 110
```

```
Ile Pro Thr Glu Trp Ser Val Val Glu Asp Leu Pro Glu Gly Pro Ala
        115                 120                 125

Val Lys Ile Gly Glu Asn Lys Asp Ala Met Asp Gly Trp Phe Arg Leu
    130                 135                 140

Glu Arg Val Ser Asp Asp Glu Phe Asn Asn Tyr Lys Leu Val Phe Cys
145                 150                 155                 160

Pro Gln Gln Ala Glu Asp Lys Cys Gly Asp Ile Gly Ile Ser Ile
                165                 170                 175

Asp His Asp Asp Gly Thr Arg Arg Leu Val Val Ser Lys Asn Lys Pro
                180                 185                 190

Leu Val Val Gln Phe Gln Lys Leu Asp Lys Glu Ser Leu Ala Lys Lys
                195                 200                 205

Asn His Gly Leu Ser Arg Ser Glu
        210                 215

<210> SEQ ID NO 3
<211> LENGTH: 100
<212> TYPE: PRT
<213> ORGANISM: Bos taurus

<400> SEQUENCE: 3

Met Lys Met Ser Arg Leu Cys Leu Ser Val Ala Leu Leu Val Leu Leu
1               5                   10                  15

Gly Thr Leu Ala Ala Ser Thr Pro Gly Cys Asp Thr Ser Asn Gln Ala
                20                  25                  30

Lys Ala Gln Arg Pro Asp Phe Cys Leu Glu Pro Pro Tyr Thr Gly Pro
            35                  40                  45

Cys Lys Ala Arg Ile Ile Arg Tyr Phe Tyr Asn Ala Lys Ala Gly Leu
        50                  55                  60

Cys Gln Thr Phe Val Tyr Gly Gly Cys Arg Ala Lys Arg Asn Asn Phe
65                  70                  75                  80

Lys Ser Ala Glu Asp Cys Met Arg Thr Cys Gly Gly Ala Ile Gly Pro
                85                  90                  95

Trp Glu Asn Leu
            100

<210> SEQ ID NO 4
<211> LENGTH: 110
<212> TYPE: PRT
<213> ORGANISM: Homo sapiens

<400> SEQUENCE: 4

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

```
<210> SEQ ID NO 5
<211> LENGTH: 39
<212> TYPE: PRT
<213> ORGANISM: Artificial Sequence
<220> FEATURE:
<223> OTHER INFORMATION: Byetta
<220> FEATURE:
<221> NAME/KEY: misc_feature
<222> LOCATION: (39)..(39)
<223> OTHER INFORMATION: Residue is amidated on the C-terminus.

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```

PROTEASE INHIBITOR-CONTAINING COMPOSITIONS, COMPOSITIONS COMPRISING SAME, AND METHODS FOR PRODUCING AND USING SAME

This application is a continuation of U.S. application Ser. No. 14/376,292, § 371 date Aug. 1, 2014, which is the U.S. National Phase Application of International Application No. PCT/IL2013/050091, filed Jan. 31, 2013, and entitled "PROTEASE INHIBITOR-CONTAINING COMPOSITIONS, COMPOSITIONS COMPRISING SAME, AND METHODS FOR PRODUCING AND USING SAME." Int. Appl. No. PCT/IL2013/050091 claims the benefit of U.S. Provisional Patent Application No. 61/632,868, filed Feb. 1, 2012, and of U.S. Provisional Patent Application No. 61/634,753, filed Mar. 6, 2012, which are incorporated herein by reference in their entirety.

FIELD

Provided herein are methods and compositions for oral administration of therapeutic proteins, improved protease inhibitor preparations, methods for producing same, and compositions comprising same.

BACKGROUND

Protein/peptide-based drugs are typically susceptible to degradation in the gastrointestinal tract and/or are not efficiently absorbed into the bloodstream from the small intestine in bioactive form. Orally delivered formulations for protein-based drugs such as insulin are being developed (Ziv et al 1994; Nissan et al 2000, Kidron et al 2004, Eldor et al 2010A, Eldor et al 2010B). One such oral insulin product is scheduled to be tested in Phase II trials and is currently being reviewed for IND status.

Trypsin inhibitors derived from soybean (*Glycine max*) are readily available and are considered to be safe for human consumption. They include SBTI (soybean trypsin inhibitor), which is composed of KTI (Kunitz Trypsin Inhibitor), which inhibits trypsin, and BBI (Bowman-Birk inhibitor), which inhibits trypsin and chymotrypsin. Such trypsin inhibitors are available for example from Sigma-Aldrich, St. Louis, Mo., USA. Methods for preparing BBI are described for example in U.S. Pat. No. 7,404,973.

SUMMARY

The present inventor has discovered that commercially available SBTI preparations produced highly variable results when used in pharmaceutical compositions. It was postulated that the activities of KTI and BBI should be individually optimized in order to improve the activity of the pharmaceutical compositions. To this end, SBTI was obtained from a commercial source as separate preparations of KTI and BBI. However, each of these preparations was found to be contaminated with the other activity. Compounding the issue, significant variability was found in the BBI activity of the preparations, particularly large-scale preparations, as evidenced by variable ability to prevent degradation of proteins (e.g. insulin) by intestinal enzymes.

Accordingly, in accordance with certain embodiments described herein, an improved method for the purification of SBTI was developed, in which each product was prepared under its own specifications to high levels of activity, and levels of high molecular weight (MW)-contaminants were minimized. In accordance with other embodiments, the process avoids the use of PEG and a second chromatography step and is characterized by higher yield. In accordance with still other embodiments, the product is particularly suitable for use in pharmaceutical compositions, for example compositions for oral administration of therapeutic proteins. In addition, in accordance with yet other embodiments, the complete separation of the KTI and BBI activities allows more precise modulation of the anti-trypsin and anti-chymotrypsin activities of pharmaceutical compositions comprising a therapeutic protein and the BBI and/or KTI, allowing for more robust and/or more reproducible in vivo activity of the pharmaceutical compositions.

It was further discovered that emulsifiers were required to conveniently prepare large-scale preparations of peptide/protein-containing drugs. However, it was necessary to empirically test whether addition of particular emulsifiers could effectively prevent precipitation in the oil-based preparations without affecting the oral efficacy of the formulations. Other described embodiments thus relate to the presence of particular emulsifiers or combinations of emulsifiers, together with improved SBTI, in oil-based pharmaceutical compositions containing therapeutic peptides and proteins.

The terms "protein" and "peptide" are used interchangeably herein. Neither term is intended to confer a limitation of the number of amino acids present, except where a limitation is explicitly indicated.

BRIEF DESCRIPTION OF THE DRAWINGS

The following figures are by way of illustrative example and are not meant to be taken as limiting the claimed invention.

FIGS. 1(A) AND 1(B) Flow diagrams of SBTI purification. FIG. 1(A): SBTI intermediate production. FIG. 1(B): Downstream purification to produce BBI and KTI.

FIG. 5(A-C) 20% SDS-PAGE of fractions from chromatography shown in FIG. 4.

FIG. 11. Testing results of various emulsifier formulations. Foam buildup score was from 1-5, where 1 indicates no foam, and 5 indicates no liquid visible because of the foam. For the suspension test, numbers 1-5 indicate full phase separation; partial phase separation with some larger oil bubbles; small oil bubble, milky consistency; no bubbles initially, with later phase separation; and stable emulsion, respectively.

FIG. 12(A)-1 to FIG. 12(A)-4; FIG. 12(B)-1; and FIG. 12(B)-2. Blood glucose profiles following administration of oral insulin formulations containing various emulsifiers. FIG. 12(A)-1. Formulation A (upper left), FIG. 12(A)-2. Formulation B (lower left), FIG. 12(A)-3. Formulation C (upper right), and FIG. 12(A)-4. Formulation D (lower right). FIG. 12(B)-1. Formulation E (left) and FIG. 12(B)-2. Formulation F (right).

FIG. 13(A) and FIG. 13(B): Patient record sheets. FIG. 13(A). Blood Sugar Record. FIG. 13(B). Questionnaire.

FIG. 14. Hypoglycemia Review Sheet. Points are awarded for each occurrence of documented hypoglycemia, with extra points given depending on the neuroglycopenic symptoms experienced or lack thereof. Examples for the definition of symptoms were as follows: visual, eyes won't focus, impaired vision, double vision; behavioral, unable to sleep, irritable, stressed out, nervous, "want to sit down and do nothing", other neurological, light-headed, dizzy, weakness, tiredness, sleepy, difficulty walking or speaking, slow responses, delayed motor skills, loss of balance; confusion, inability to perform simple math, feeling "out of it". No points are awarded if there were autonomic symptoms that gave adequate warning of impending hypoglycemia, even if some neuroglycopenic symptoms were also present. Additional points are given for the need for outside help to either recognize or treat the event.

DETAILED DESCRIPTION OF THE EMBODIMENTS

Figure 1B:
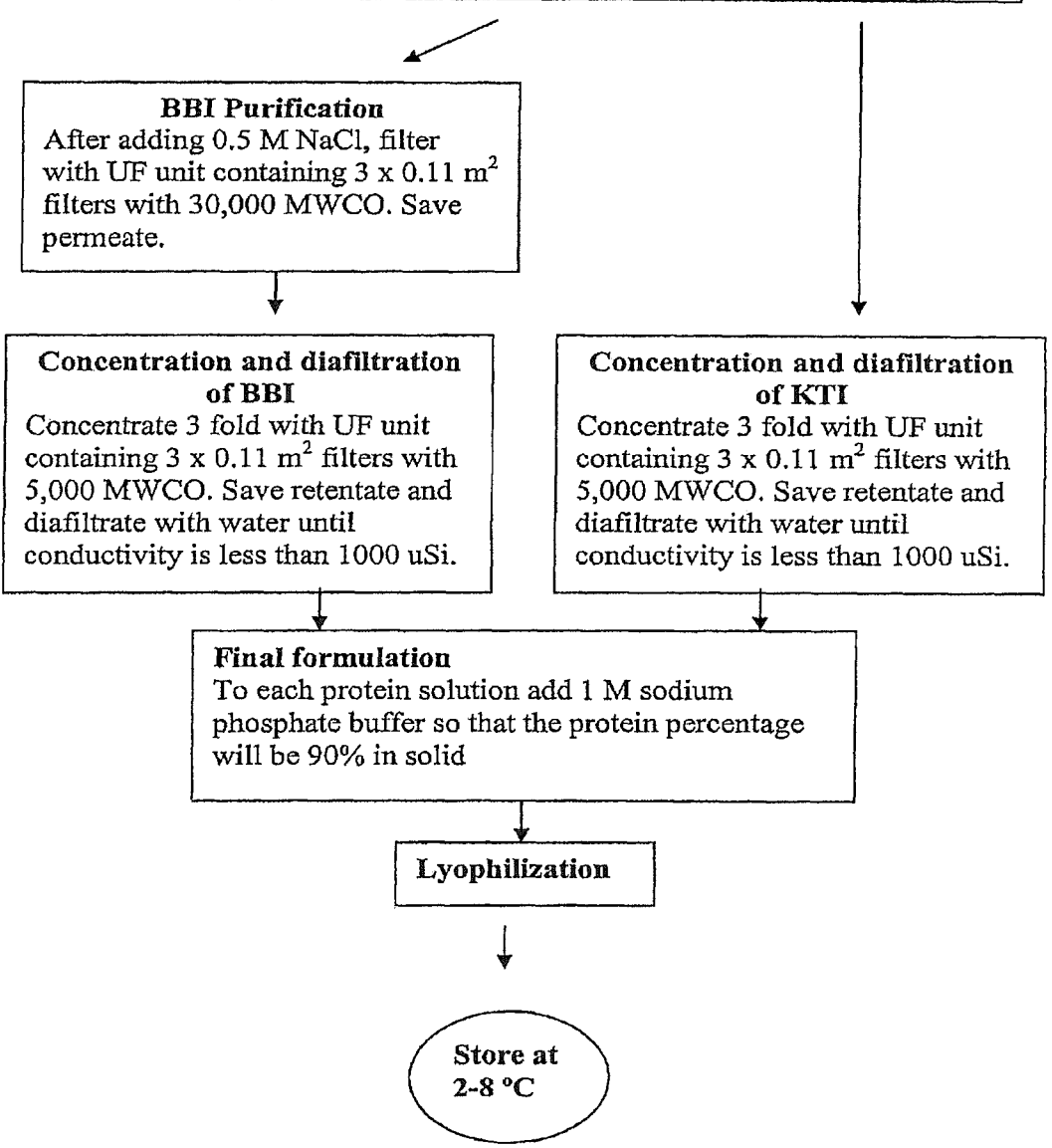

In one aspect, a BBI isolated from a soybean product is provided, wherein the BBI is at least 85% pure as measured, in various embodiments, by sodium dodecyl sulfate polyacrylamide gel electrophoresis (SDS-PAGE), Brilliant Blue staining, or imager quantitation. In certain embodiments, the soybean product is soy flour.

In yet another aspect is provided a BBI isolated from soy flour, wherein the protein content of the BBI is greater than 95% by BCA (bicinchoninic acid) assay.

In yet another aspect is provided a BBI isolated from soy flour, wherein the BBI contains less than 0.1% high-MW contaminants, for example as assessed by SDS-PAGE and imager quantitation.

In other embodiments, the ratio of the anti-trypsin activity to the anti-chymotrypsin activity present in the isolated BBI is between 1.5:1 and 1:1 inclusive. In more specific embodiments, the ratio may be between 1.4:1-1.1:1, inclusive. In more specific embodiments, the ratio may be between 1.35:1-1.2:1, inclusive. In more specific embodiments, the ratio may be 1.28:1.

Unless indicated otherwise, anti-chymotrypsin activity referred to herein is measured using chymotrypsin having an activity of 40 BTEE units per mg. of chymotrypsin, and is expressed in mg. of chymotrypsin inhibited per mg. of protein being tested. BTEE refers to N-Benzoyl-L-Tyrosine Ethyl Ester (see the directions for Sigma-Aldrich Product No. B6125).

Unless indicated otherwise, anti-trypsin activity referred to herein is measured using trypsin having an activity of 10,000 BAEE units per mg. of trypsin, and is expressed in mg. of trypsin inhibited per mg. of protein being tested. BAEE refers to Na-Benzoyl-L-Arginine Ethyl Ester Solution (see the directions for Sigma-Aldrich Product No. B4500). For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241:3955; and Y. Birk, 1976, Meth. Enzymol. 45:700.

Those skilled in the art will appreciate that each of the above purity requirements, regarding its protein content, level of contaminants, or potency, is typically assessed prior to the BBI being mixed with one or more other components of the pharmaceutical composition.

In an additional aspect, a KTI3 isolated from soy flour is provided, wherein the KTI3 is at least 85% pure as measured, in various embodiments, by SDS-PAGE, Brilliant Blue staining, or imager quantitation.

In yet another aspect is provided a KTI3 isolated from soy flour, wherein the protein content of the KTI3 is greater than 95% as measured by BCA assay.

In yet another aspect is provided a KTI3 isolated from soy flour, wherein the KTI3 contains less than 0.1% high-MW contaminants, for example as assessed by SDS-PAGE and imager quantitation.

Those skilled in the art will appreciate that each of the above purity requirements, regarding its protein content, level of contaminants, or potency, is typically assessed prior to the KTI3 being mixed with one or more other components of the pharmaceutical composition.

In certain embodiments, the KTI3-containing pharmaceutical composition further comprises a BBI that meets at least one of the above purity requirements prior to its being mixed with one or more other components of the pharmaceutical composition.

In certain embodiments, the above-described pharmaceutical compositions are formulated for oral administration. In more specific embodiments, the pharmaceutical composition further comprises a coating that resists degradation in the stomach. In even more specific embodiments, the coating is a pH-sensitive capsule, or alternatively, is a soft gelatin capsule.

In other embodiments, the above-described pharmaceutical compositions further comprise a therapeutic protein of up to 100 kilodaltons as an active ingredient. In other embodiments, the active ingredient is a non-protein molecule that is sensitive to degradation or inactivation in the human digestive tract.

In another embodiment, an oral pharmaceutical composition is provided, comprising an oil-based liquid formulation, wherein the oil-based liquid formulation comprises a therapeutic protein of up to 100 kilodaltons (kDa), a chelator of divalent cations, and an isolated BBI. In other embodiments, the liquid formulation consists essentially of a therapeutic protein of up to 100 kDa, a chelator of divalent cations, an isolated BBI, and an oil. In other embodiments, the liquid formulation consists essentially of a therapeutic protein of up to 100 kDa, a chelator of divalent cations, an isolated BBI, an oil, and an emulsifier. In other embodiments, the liquid formulation consists essentially of a therapeutic protein of up to 100 kDa, a chelator of divalent cations, an isolated BBI, an oil, and two emulsifiers.

In another aspect is provided an oral pharmaceutical composition comprising an oil-based liquid formulation, wherein the oil-based liquid formulation comprises a therapeutic protein of up to 100 kDa, a chelator of divalent cations, and a soybean-derived BBI, wherein said liquid formulation contains less than 0.05% of soybean-derived substances having a MW of greater than 30,000.

In another aspect is provided an oral pharmaceutical composition comprising an oil-based liquid formulation, wherein the oil-based liquid formulation comprises a therapeutic protein of up to 100 kDa and a chelator of divalent cations, and said liquid formulation has an anti-chymotrypsin activity of at least 50 mg chymotrypsin inhibited per ml. of the liquid formulation. In other embodiments, the liquid formulation has an anti-chymotrypsin activity of at least 35, 40, 45, 55 or 60 mg. chymotrypsin inhibited per ml. of the liquid formulation. In still other embodiments, the liquid formulation has an anti-chymotrypsin activity in the range of 35-70, 40-70, 45-70, 50-70, or 40-60 mg. of chymotrypsin inhibited per ml. of the liquid formulation. In other embodiments, the liquid formulation further comprises an anti-trypsin activity of at least 25 mg. of trypsin inhibited per ml. of the liquid formulation. In other embodiments, the liquid formulation further comprises an anti-trypsin activity of at least 30, 35, 40, 45, or 50 mg. trypsin inhibited per ml. of the liquid formulation. Alternatively, the liquid formulation further comprises an anti-trypsin activity in the range of 25-50, 30-50, 35-50, 25-40, or 25-45 mg. trypsin inhibited per ml. of the liquid formulation. Alternatively, the liquid formulation further comprises an anti-trypsin activity of at least 20 mg. trypsin inhibited per ml. of the liquid formulation.

In another aspect is provided a method for making a pharmaceutical composition, comprising the steps of (a) providing a preparation of isolated BBI, a therapeutic protein of up to 100 kilodaltons, and a chelator of divalent cations; and (b) mixing said isolated BBI, therapeutic protein, and chelator into an oil-based liquid formulation. Each of the embodiments described herein of the identity, purity, and potency of isolated BBI may be incorporated into this method. In addition, each of the embodiments described herein of the other ingredients, and of additional ingredients that may be present, may be incorporated into this method. In other embodiments, a pharmaceutical composition made by this method is provided.

In another aspect is provided a method for making a pharmaceutical composition, comprising the step of mixing an isolated BBI, a therapeutic protein of up to 100 kilodaltons, and a chelator of divalent cations into an oil-based liquid formulation. Each of the embodiments described herein of the identity, purity, and potency of isolated BBI may be incorporated into this method. In addition, each of the embodiments described herein of the other ingredients, and of additional ingredients that may be present, may be incorporated into this method. In other embodiments, a pharmaceutical composition made by this method is provided.

"Liquid" as used herein refers to a composition that has a viscosity within the range of 1-1000 millipascal seconds, inclusive, at 20° C. Fish oil, for instance, is a liquid under ambient conditions. The term includes oil-based solutions, suspensions, and combinations thereof.

"Isolated" BBI as used herein refers to a preparation enriched in BBI relative to other components. In more specific embodiments, BBI refers to Bowman-Birk inhibitor; Uniprot number P01055 [database accessed on Jan. 28, 2013]).

A representative precursor sequence of BBI is:

```
                                        (SEQ ID NO: 1)
MVVLKVCLVL LFLVGGTTSA NLRLSKLGLL MKSDHQHSND

DESSKPCCDQ CACTKSNPPQ CRCSDMRLNS CHSACKSCIC

ALSYPAQCFC VDITDFCYEP CKPSEDDKEN.
```

Of these 110 residues, residues 1-19 are the signal peptide, 20-39 are a propeptide, and the mature chain BBI chain is composed of residues 40-110 (71 AA).

In various embodiments, the preparation of BBI utilized in the described methods and compositions is at least 85%, 90%, 92%, 94%, or 95% pure as assessed by SDS-PAGE, Brilliant Blue staining, or imager quantitation (e.g. according to the protocol described herein). In the context of a pharmaceutical composition, this value refers to characteristics of the BBI prior to its being mixed with one or more other components of the pharmaceutical composition. In alternative embodiments, SDS-PAGE and silver staining, optionally followed by imager quantitation, may be utilized.

In other embodiments, the isolated BBI has an anti-chymotrypsin activity of at least 0.8, 0.9, 1.0, 1.1, 1.2, 1.3, or 1.4 mg. chymotrypsin inhibited per mg. inhibitor. In other embodiments, the anti-chymotrypsin activity is in the range of 0.8-1.8, 0.9-1.8, 1.0-1.8, 1.1-1.8, 1.2-1.8, 1.3-1.8, or 1.4-1.8 mg. chymotrypsin inhibited per mg. inhibitor. In more specific embodiments, the activity is 0.8-1.8 mg. chymotrypsin inhibited per mg. inhibitor. In other embodiments, the activity is in the range of 0.8-1.5 mg. chymotrypsin inhibited per mg. inhibitor. In the context of a pharmaceutical composition, this value refers to characteristics of the BBI prior to its being mixed with one or more other components of the pharmaceutical composition.

In various embodiments, the BBI preparation contains 5% or less KTI as assessed by SDS-PAGE, Brilliant Blue staining, or imager quantitation (according to the protocol described herein). In alternative embodiments, SDS-PAGE and silver staining may be utilized.

In more specific embodiments, KTI as used herein refers to KTI3 (Uniprot number P01070; database accessed on Jan. 3, 2013). A representative precursor sequence of KTI3 is:

```
                                         SEQ ID NO: 2)
MKSTIFFLFL FCAFTTSYLP SAIADFVLDN EGNPLENGGT

YYILSDITAF GGIRAAPTGN ERCPLTVVQS RNELDKGIGT

IISSPYRIRF IAEGHPLSLK FDSFAVIMLC VGIPTEWSVV

EDLPEGPAVK IGENKDAMDG WFRLERVSDD EFNNYKLVFC

PQQAEDDKCG DIGISIDHDD GTRRLVVSKN KPLVVQFQKL

DKESLAKKNH GLSRSE
```

Of the above sequence, residues 1-24 are the signal peptide, 206-216 are the propeptide, and the mature KTI chain is composed of residues 25-205 (181 AA).

In other embodiments, the protein content of the BBI preparation is greater than 95% by BCA assay (for example using the Micro BCA Protein Assay Kit [cat. #23225, Thermo Scientific Rockford, Ill.]). In the context of a pharmaceutical composition, this value refers to its characteristics prior to its being mixed with one or more other components of the pharmaceutical composition. In other embodiments, the BBI preparation contains less than 0.1% high-MW contaminants (in other words, substances having a MW of greater than 30,000). In other embodiments, the BBI has been isolated without the use of polyethyleneglycol (PEG).

In other embodiments, the isolated BBI in the described methods and compositions is a recombinant BBI, for example BBI produced by a microorganism such as a bacterium that has been engineered to express it and subsequently isolated. In still other embodiments, the BBI is a synthetic BBI. An example of a synthetic BBI is BBI that has been produced in a cell-free apparatus such as a peptide synthesizer. Peptide synthesizers, for example automated peptide synthesizers, are well known in the art and are available commercially. Pharmaceutical compositions comprising recombinant BBI are also provided herein. Pharmaceutical compositions comprising synthetic BBI are also provided herein.

In certain embodiments, the described BBI is the only protease inhibitor in the described methods and compositions. While lower-potency SBTI requires an additional protease inhibitor, e.g. aprotinin, to efficiently protect certain therapeutic proteins in the human digestive tract, the described isolated BBI is believed to be capable of reducing the need for additional protease inhibitors in this regard.

Additional Protease Inhibitors

In certain embodiments, the oil-based liquid formulation utilized in the described methods and compositions further comprises a trypsin inhibitor other than the isolated BBI. In other embodiments, the oil-based liquid formulation utilized in the described methods and compositions further comprises a trypsin inhibitor other than the isolated KTI3. Those skilled in the art will appreciate in light of the present disclosure that a variety of trypsin inhibitors may be utilized. In the case of trypsin inhibitors that are proteins, the size will typically be up to 100 kDa.

As used herein, the term "trypsin inhibitor" refers to any agent capable of inhibiting the action of trypsin on a substrate. The ability of an agent to inhibit trypsin can be measured using assays well known in the art.

Some trypsin inhibitors known in the art are specific to trypsin, while others inhibit trypsin and other proteases such as chymotrypsin. Trypsin inhibitors can be derived from animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678. A trypsin inhibitor can also be an arginine or lysine mimic or other synthetic compound: for example arylguanidine, benzamidine, 3,4-dichloroisocoumarin, diisopropylfluorophosphate, gabexate mesylate, or phenylmethanesulfonyl fluoride. As used herein, an arginine or lysine mimic is a compound that is capable of binding to the $P^1$ pocket of trypsin and/or interfering with trypsin active site function.

In certain embodiments, the additional trypsin inhibitor utilized in the described methods and compositions is selected from the group consisting of lima bean trypsin inhibitor, aprotinin, (a.k.a. pancreatic trypsin inhibitor or basic pancreatic trypsin inhibitor [BPTI]; Uniprot No. P00974 [database accessed on Jan. 2, 2013]), Kazal inhibitor (pancreatic secretory trypsin inhibitor), Kazal inhibitor (pancreatic secretory trypsin inhibitor), ovomucoid, Alpha 1-antitrypsin, Cortisol binding globulin, Centerin ([SERPINA9/GCET1 (germinal centre B-cell-expressed transcript 1)], PI-6 (Sun et al 1995), PI-8 (Sprecher et al 1995), Bomapin, a clade A serpin [for example Serpina3 (NCBI Gene ID: 12), Serpina6 (NCBI Gene ID: 866), Serpina12 (NCBI Gene ID: 145264); Serpina10 (NCBI Gene ID: 51156); Serpina7 (NCBI Gene ID: 6906); Serpina9 (NCBI Gene ID: 327657); Serpina11 (NCBI Gene ID: 256394); Serpina13 (NCBI Gene ID: 388007); Serpina2 (NCBI Gene ID: 390502); and Serpina4 (NCBI Gene ID: 5104)] Yukopin (Serpinb12; Gene ID: 89777), antipain, benzamidine, 3,4-dichloroisocoumarin, diisopropylfluorophosphate, and gabexate mesylate. In other embodiments, one of the above inhibitors is selected.

A representative precursor sequence of aprotinin is:

```
                                           (SEQ ID NO: 3)
MKMSRLCLSV ALLVLLGTLA ASTPGCDTSN QAKAQRPDFC

LEPPYTGPCK ARIIRYFYNA KAGLCQTFVY GGCRAKRNNF

KSAEDCMRTC GGAIGPWENL.
```

Of these 100 residues, residues 1-21 are the signal peptide, 22-35 and 94-100 are propeptides, and the mature chain BBI chain is composed of residues 36-93 (58 AA).

In other embodiments, an oil-based liquid formulation utilized in the described methods and compositions comprises both isolated BBI and isolated KTI, in more specific embodiments both isolated BBI and isolated KTI3. "Isolated" KTI as used herein refers to a preparation enriched in KTI relative to other components. In various embodiments, the preparation of KTI utilized in the described methods and compositions is at least 85% pure as assessed by SDS-PAGE, Brilliant Blue staining, or imager quantitation (e.g. according to the protocol described herein). In other embodiments, the protein content of the KTI preparation is greater than 95% by BCA assay. In the context of a pharmaceutical composition, these values refer to characteristics of the KTI prior to its being mixed with one or more other components of the pharmaceutical composition. In other embodiments, the KTI preparation contains 5% or less BBI as assessed by SDS-PAGE. In other embodiments, the KTI preparation contains less than 0.1% high-MW contaminants (in other words, substances having a MW of greater than 30,000). In other embodiments, the KTI has been isolated without the use of PEG.

In still more specific embodiments, the described methods and compositions comprise the described BBI and KTI, in more specific embodiments BBI and KTI3, as the only protease inhibitors. In other embodiments, the described methods and compositions comprise KTI and aprotinin, in more specific embodiments KTI3 and aprotinin, as the only protease inhibitors. In other embodiments, isolated BBI, isolated KTI, and aprotinin are all present in the oil-based liquid formulation.

In other embodiments, the isolated KTI3 has an activity of at least 0.8, 0.9, 1.0, 1.1, 1.2, or 1.3 mg. trypsin inhibited per mg. inhibitor. In other embodiments, the activity of the KTI3 is in the range of 0.8-1.8, 0.9-1.8, 1.0-1.8, 1.1-1.8, 1.2-1.8, or 1.3-1.8 mg. trypsin inhibited per mg. inhibitor. In more particular embodiments, the activity of the KTI3 is 0.8-1.7 mg. trypsin inhibited per mg. inhibitor. In other embodiments, the activity is range of 0.8-1.4 mg. trypsin inhibited per mg. inhibitor.

In other preferred embodiments, the isolated KTI is a recombinant KTI, for example KTI produced by a microorganism such as a bacterium that has been engineered to express it. In still other preferred embodiments, the KTI is a synthetic KTI. An example of a synthetic KTI is KTI that has been produced in a cell-free apparatus such as a peptide synthesizer.

Other embodiments concern the ratio of the anti-chymotrypsin activity present in the described pharmaceutical composition to the anti-trypsin activity of the composition. In some embodiments, this parameter is between 1.5:1 and 1:1 inclusive. In more specific embodiments, the ratio may be between 1.4:1-1.1:1, inclusive. In more specific embodiments, the ratio may be between 1.35:1-1.2:1, inclusive.

In certain embodiments, the BBI utilized in the described methods and compositions, and/or KTI, if present, has been stored with a preservative. In other embodiments, the BBI and/or KTI has been prepared and stored without use of a preservative.

In certain embodiments, the BBI utilized in the described methods and compositions, and/or the KTI, if present, is obtained from soy flour. The term "soy flour" refers to flour obtained from the species *Glycine max*. In other embodiments, any species from the genus Glycine may be utilized. Methods for obtaining soy flour are well known in the art. The described methods are believed be applicable to any type of soy flour, no matter how it was produced.

Therapeutic Proteins

Therapeutic proteins for compositions and methods described herein are in some embodiments isolated prior to inclusion in the described pharmaceutical compositions. "Isolated" in this regard excludes provision of the therapeutic protein as a homogenized tissue preparation or other form containing substantial amounts of contaminating proteins. A preferred example of an isolated protein or peptide is a recombinant protein or peptide. An even more preferred embodiment is a synthetic protein, in other words a protein produced in a cell-free apparatus. Those skilled in the art will appreciate in light of the present disclosure that both wild-type and mutated therapeutic proteins may be utilized.

Certain proteins and peptides are known to be specific inhibitors of trypsin and/or chymotrypsin, including but not limited to those described herein as being trypsin and/or chymotrypsin inhibitors. Such proteins are not intended for use as the therapeutic component in the described compositions, and are excluded from the definition of "therapeutic proteins" as used herein.

Those of skill in the art will appreciate in light of the present disclosure that a variety of therapeutic proteins may be used in the described methods and compositions. In certain embodiments, the therapeutic protein is up to 100 kilodaltons (kDa) in size, typically between 1-100 kDa, inclusive. In more specific embodiments, the size is up to 90 kDa. In other embodiments, the size is up to 80 kDa. In other embodiments, the size is up to 70 kDa. In other embodiments, the size is up to 60 kDa. In other embodiments, the size is up to 50 kDa. Preferably, the size is between 1-90 kDa, inclusive. In other embodiments, the size is between 1-80 kDa, inclusive. In other embodiments, the size is between 1-70 kDa, inclusive. In other embodiments, the size is between 1-60 kDa, inclusive. In other embodiments, the size is between 1-50 kDa, inclusive.

Therapeutic proteins suitable for use herein include derivatives that are modified (i.e., by the covalent attachment of a non-amino acid moiety to the protein). For example, but not by way of limitation, the protein includes proteins that have been modified, e.g., by glycosylation, acetylation, PEGylation, phosphorylation, amidation, or derivatization by known protecting/blocking groups. High-MW PEG can be attached to therapeutic proteins with or without a multifunctional linker either through site-specific conjugation of the PEG to the N- or C-terminus thereof or via epsilon-amino groups present on lysine residues. Additionally, the derivative may contain one or more non-classical amino acids.

In certain, more specific, embodiments, the therapeutic protein utilized in the described methods and compositions is selected from the group consisting of insulin, influenza hemagglutinin, influenza neuraminidase, glucagon, interferon gamma, interferon beta, interferon alpha, growth hormone, erythropoietin, GLP-1, a GLP-1 analogue, granulocyte colony stimulating factor (G-CSF), renin, growth hormone releasing factor, parathyroid hormone, thyroid stimulating hormone, follicle stimulating hormone, calcitonin, luteinizing hormone, glucagon, a clotting factor (for example factor VII, factor VIIIC, factor DC, tissue factor (TF), and thrombin), an anti-clotting factor (for example Protein C), atrial natriuretic factor, surfactant protein A (SP-A), surfactant protein B (SP-B), surfactant protein C (SP-C), surfactant protein D (SP-D), a plasminogen activator (for example urokinase or human urine or tissue-type plasminogen activator (t-PA)), bombesin, hemopoietic growth factor (a.k.a. colony-stimulating factor, multiple), a tumor necrosis factor (TNF) protein (for example TNF-alpha, TNF-beta, TNF beta-2, 4-1BBL), enkephalinase, RANTES (regulated on activation normally T-cell expressed and secreted), human macrophage inflammatory protein (MIP-1-alpha), serum albumin, Mullerian-inhibiting substance, relaxin, mouse gonadotropin-releasing hormone, DNase, inhibin, activin, vascular endothelial growth factor (VEGF), a neurotrophic factor (for example brain-derived neurotrophic factor [BDNF]), neurotrophin-3, -4, -5, or -6 (NT-3, NT-4, NT-5, or NT-6), nerve growth factor, platelet-derived growth factor (PDGF), a fibroblast growth factor (for example alpha-FGF and beta-FGF), a transforming growth factor (TGF) (for example TGF-alpha and TGF-beta, including TGF-1, TGF-2, TGF-3, TGF-4, and TGF-5), insulin-like growth factor-I and -II (IGF-I and IGF-II), des (1-3)-IGF-I (brain IGF-I), insulin-like growth factor binding proteins (including IGFBP-1, IGFBP-2, IGFBP-3, IGFBP-4, IGFBP-5, and IGFBP-6), a keratinocyte growth factor, an osteoinductive factor, bone morphogenetic protein (BMP)-2, BMP-7, a colony stimulating factor (CSF) (for example M-CSF and GM-CSF), an interleukin (IL), (for example IL-1 to IL-13 and IL-15, IL-18, and IL-23), superoxide dismutase, decay accelerating factor, a chemokine family member (for example the eotaxins and MCP-1), and a complement factor (for example C3 and C5).

In still more specific embodiments, the therapeutic protein is insulin. Alternatively, the therapeutic protein may be a GLP-1 inhibitor. In a more specific embodiment, the therapeutic protein is exenatide. In other embodiments, both insulin and exenatide are present in the described composition. In other embodiments, the liquid formulation consists essentially of insulin, exenatide, a chelator of divalent cations, an isolated BBI, and an oil. In other embodiments, the liquid formulation consists essentially of insulin, exenatide, a chelator of divalent cations, an isolated BBI, at least one emulsifier, and an oil. In still other embodiments, the liquid formulation consists essentially of insulin, exenatide, a chelator of divalent cations, an isolated KTI3, aprotinin, and an oil. In yet embodiments, the liquid formulation consists essentially of insulin, exenatide, a chelator of divalent cations, an isolated KTI3, aprotinin, at least one emulsifier, and an oil.

A person skilled in the art will appreciate in light of the present disclosure that various types of insulin are suitable for the described methods and compositions. Exemplary insulin proteins include but are not limited to both wild-type and mutated insulin proteins, including synthetic human insulin, synthetic bovine insulin, synthetic porcine insulin, synthetic whale insulin, and metal complexes of insulin, such as zinc complexes of insulin, protamine zinc insulin, and globin zinc.

Various classes of insulin may also be utilized, for example fast-acting insulin, lente insulin, semilente insulin, ultralente insulin, NPH insulin, glargine insulin, lispro insulin, aspart insulin, or combinations of two or more of the above types of insulin.

In a particularly preferred embodiment, the insulin of the described methods and compositions is wild-type human insulin (Uniprot ID P01308; SEQ ID NO: 4). Of the 110 amino acids, 1-24 is the signal peptide, 25-54 forms the insulin B chain, 57-87 forms C peptide, and 90-110 forms the insulin A chain. In one preferred embodiment, human insulin is produced as a recombinant protein in bacterial cells. In another preferred embodiment, human insulin is produced synthetically.

GLP-1 analogues are also referred to in the art as GLP-1 mimetics. A person of skill in the art will appreciate in light of the present disclosure that the described compositions may include at least one of the following GLP-1 analogues: exenatide (Byetta™; CAS no. 141732-76-5; SEQ ID NO: 5), lixisenatide (CAS no. 320367-13-3), liraglutide (CAS no. 204656-20-2), exendin-9 (CAS no. 133514-43-9), AC3174 ([Leu(14)]exendin-4, Amylin Pharmaceuticals, Inc.), taspoglutide (CAS no. 275371-94-3), albiglutide (CAS no. 782500-75-8), semaglutide (CAS no. 910463-68-2), LY2189265 (Dulaglutide™; CAS no. 923950-08-7), and CJC-1134-PC (a modified Exendin-4 analogue conjugated to recombinant human albumin manufactured by ConjuChem™). All CAS records were accessed on Dec. 19, 2011. Thus, in certain embodiments, the described method or composition utilizes any of the above-listed GLP-1 analogues. In other embodiments, one of the above-listed GLP-1 analogues is selected. Those of skill in the art will appreciate in light of the findings presented herein that other GLP-1 analogues can also be utilized in the described methods and compositions.

Emulsifiers

"Weight/weight" percentages of emulsifiers and detergents referred to herein utilize the amount of oil base in the formulation, for example fish oil, as the denominator; thus, 60 mg of Gelucire in 500 mg fish oil is considered as 12% w/w, regardless of the weight of the other components. Similarly, 50 mg. Tween-80 mixed with 500 mg fish oil is considered as 10% Tween-80.

In certain embodiments, the oil-based liquid formulation utilized in the described methods and pharmaceutical compositions, or in other embodiments, each of the oil-based liquid formulation that is present, comprises, in addition to the therapeutic protein, chelator, and BBI, a polyethylene glycol (PEG) ester of a fatty acid, for example a PEG ester of a monoglyceride, a diglyceride, a triglyceride, or a mixture thereof. In more specific embodiments, the PEG ester may be provided as a mixture of (a) a free monoacylglycerol, a free diacylglycerol, a free triacylglycerol, or a mixture thereof; and (b) a PEG ester of a fatty acid, for example a PEG ester of a monoglyceride, a diglyceride, a triglyceride, or a mixture thereof. In this regard, each of the terms "monoacylglycerol", "diacylglycerol", and "triacylglycerol" need not refer to a single compound, but rather can include mixtures of compounds, for example mixtures of monoacylglycerols, diacylglycerols, or triacylglycerols having fatty acids of varying lengths. In certain preferred embodiments, monoacylglycerols, diacylglycerols, or triacylglycerols utilized in the described methods and compositions, for example those used to general PEG esters, are from an oil source that is Generally Recognized As Safe (GRAS). Examples of GRAS oils are coconut oil, corn oil, peanut oil, soybean oil, Myvacet 9-45 (Diacetylated monoacylglycerols of C-18 fatty acids). A more specific embodiment of (a) is a mixture of $C_8$-$C_{18}$ monoacylglycerols, diacylglycerols, and triacylglycerols. A more specific embodiment of component (b) is a mixture of PEG monoesters and diesters of one or more $C_8$-$C_{18}$ fatty acids.

In more specific embodiments, the liquid formulation further comprises, in addition to the PEG ester of a fatty acid, a free PEG. In still more specific embodiments, an additional non-ionic detergent, for example a polysorbate-based detergent, is present in addition to the PEG ester and free PEG.

In a still more specific embodiment of the described methods and compositions, a liquid formulation comprises: (a) a mixture of $C_8$-$C_{18}$ monoacylglycerols, diacylglycerols, and triacylglycerols; (b) PEG-32 monoesters and diesters of a mixture of $C_8$-$C_{18}$ fatty acids; and (c) free PEG-32. In even more specific embodiments, the weight/weight ratio of component (a) to the sum of components (b)+(c) is between 10:90-30:70 inclusive; more specifically between 15:85-25:75 inclusive; more specifically 20:80. In certain embodiments, components (a)-(c) together constitute 8-16% weight/weight inclusive of the oil-based liquid formulation. In more specific embodiments, the amount is 9-15% inclusive. In more specific embodiments, the amount is 10-14% inclusive. In more specific embodiments, the amount is 11-13% inclusive. In more specific embodiments, the amount is 12%.

In other embodiments, an oil-based liquid formulation utilized in the described methods and pharmaceutical compositions comprises, in addition to the therapeutic protein, chelator, and BBI, a self-emulsifying component. While some embodiments of self-emulsifying components are the mixtures of components described in the preceding paragraphs, these mixtures do not limit the definition of the term "self-emulsifying components" as used herein. "Self-emulsifying component" as used herein refers to a component that spontaneously forms an emulsion. Typically, such components will form an emulsion on contact with aqueous media, forming a fine dispersion i.e. a microemulsion (SMEDDS). Certain embodiments of such components comprise a triacylglycerol mixture of triacylglycerols and a high hydrophile/lipophile balance (HLB; see Griffin W C: "Calculation of HLB Values of Non-Ionic Surfactants," J Soc Cosmetic Chemists 5:259 (1954)) surfactant. Other embodiments of the self-emulsifying component have a waxy, semi solid consistency.

Preferably, the HLB of a self-emulsifying component utilized in the described methods and compositions is 10 or greater. In other embodiments, it is between 11-19 inclusive. In other embodiments, it is between 12-18 inclusive. In other embodiments, it is between 12-17 inclusive. In other embodiments, it is between 12-16 inclusive, which is indicative of an oil-in-water (O/W) emulsifier. In other embodiments, it is between 13-15 inclusive. In other embodiments, it is 14. Still more specific embodiments of self-emulsifying components have an HLB of 12-16 inclusive and comprise medium- and long-chain triacylglycerols conjugated to PEG, free triacylglycerols, and free PEG. In other embodiments, the self-emulsifying component has an HLB of 12-16 inclusive and consists of a mixture of medium- and long-chain triacylglycerols conjugated to PEG, free triacylglycerols, and free PEG. In other embodiments, the self-emulsifying component has an HLB of 14 and comprises medium- and long-chain triacylglycerols conjugated to PEG, free triacylglycerols, and free PEG. In other embodiments, the self-emulsifying component has an HLB of 14 and consists of a mixture of medium- and long-chain triacylglycerols conjugated to PEG, free triacylglycerols, and free PEG.

Certain, more specific embodiments utilize self-emulsifying components that comprise (a) a monoacylglycerol, a diacylglycerol, a triacylglycerol, or a mixture thereof; and (b) a polyethylene glycol (PEG) ester of a fatty acid. In this regard, each of the terms "monoacylglycerol", "diacylglycerol", and "triacylglycerol" need not refer to a single compound, but rather can include mixtures of compounds, for example mixtures of monoacylglycerols, diacylglycerols, or triacylglycerols having fatty acids of varying lengths. A more specific embodiment is a mixture of $C_8$-$C_{18}$ monoacylglycerols, diacylglycerols, and triacylglycerols. A more specific embodiment of component (b) is a mixture of PEG monoesters and diesters of a mixture of $C_8$-$C_{18}$ fatty acids.

In other, more specific embodiments, the self-emulsifying component further comprises free PEG.

Certain PEG moieties for use in the described compositions and methods contain between 5-100 monomers. In more specific embodiments, the PEG may contain between 15-50 monomers. In still more specific embodiments, the PEG may contain between 25-40 monomers. In more specific embodiments, the PEG may contain 32 monomers.

In still more specific embodiments of the described methods and compositions, a self-emulsifying component used therein comprises: (a) a mixture of $C_8$-$C_{18}$ monoacylglycerols, diacylglycerols, and triacylglycerols; (b) PEG-32 monoesters and diesters of a mixture of $C_8$-$C_{18}$ fatty acids; and (c) free PEG-32; and the weight/weight ratio of component (a) to components (b)+(c) is 20:80. In certain embodiments, such a component constitutes 8-16% weight/weight inclusive of the oil-based liquid formulation. In more specific embodiments, the amount is 9-15% inclusive. In more specific embodiments, the amount is 10-14% inclusive. In more specific embodiments, the amount is 11-13% inclusive. In more specific embodiments, the amount is 12%.

Examples of self-emulsifying components meeting the above specifications are Gelucire™ 44/14, Gelucire™ 53/10, and Gelucire™ 50/13. A more specific embodiment is Gelucire™ 44/14. The suffixes 44 and 14 refer respectively to its melting point and its hydrophilic/lypophilic balance (HLB). Gelucire™ 44/14 (Gattefossé SAS, Saint-Priest, France) is obtained by polyglycolysis of hydrogenated coconut oil (medium- and long-chain triacylglycerols with PEG-32. It has a hydrophile/lipophile balance of 14. It is composed of a defined admixture of $C_8$-$C_{18}$ mono-, di- and triacylglycerols (20% w/w); PEG-32 mono- and diesters and free PEG-32 (80% w/w). The main fatty acid present is lauric acid, accounting for 45% on average of the total fatty acid content. It is a solid dispersion composed of a PEG ester fraction under a lamellar phase of 120 Å with a helical conformation and an acylglycerol fraction under a hexagonal packing. The main products of simulated gastrointestinal lipolysis of Gelucire™ 44/14 are PEG-32 mono and diesters. In more specific embodiments, the described compositions comprise about 12% Gelucire 44/14 as the only emulsifier, or, in other embodiments, together with another emulsifier. In other embodiments, the described compositions comprise about 12% Gelucire 44/14 and about 10% Tween-80.

Non-Ionic Detergents

In certain embodiments, an oil-based liquid formulation utilized in the described methods and pharmaceutical compositions further comprises a non-ionic detergent in addition to the self-emulsifying component. In certain embodiments, the non-ionic detergent is selected from the group consisting of polysorbate-20, polysorbate-40, polysorbate-80, lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose, carboxymethyl cellulose, n-octylglucoside, n-dodecylglucoside, n-dodecylmaltoside, octanoyl-N-methylglucamide, decanoyl-N-methylglucamide, Triton™-X-100, Triton™-X-114, Thesit™, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), and N-dodecyl=N,N-dimethyl-3-ammonio-1-propane sulfonate. In other embodiments, one of the above-listed non-ionic detergents is selected.

In certain, more specific embodiments, a non-ionic detergent used in the described methods and compositions is a polysorbate-based detergent. Examples of polysorbate-based detergents are detergents derived by covalently bonding polyethoxylated sorbitan to a fatty acid. More specific embodiments of polysorbate-based detergents are polysorbate-20, polysorbate-40, and polysorbate-80.

For example, polysorbate 80 (Tween-80) is a non-ionic detergent derived from polyethoxylated sorbitan and oleic acid and having the following structure:

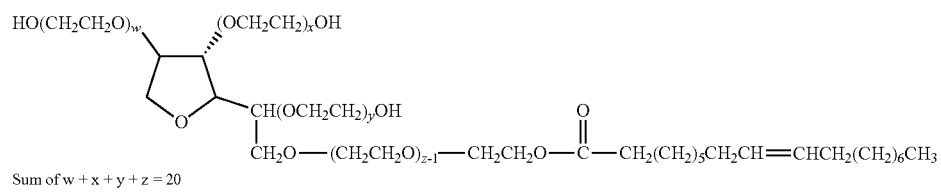

Sum of w + x + y + z = 20

In the case of polysorbate 80, the moiety shown on the right side is a mixture of fatty acids, containing 60-70% oleic acid (as depicted), with the balance being primarily linoleic, palmitic, and stearic acids.

In a more specific embodiment, the polysorbate 80 constitutes 3-15% weight/weight inclusive of an oil-based liquid formulation used in the described methods and compositions. In a more specific embodiment, the percentage is 5-14% inclusive. In a more specific embodiment, the percentage is 7-12% inclusive. In more specific embodiments, the percentage is 10%, or alternatively 5%.

Chelators of Divalent Cations

The chelator of divalent cations utilized in the described methods and compositions is, in one embodiment, any physiologically acceptable compound having a high affinity for at least one of calcium, magnesium, and manganese ions. In another embodiment, the chelator is selected from the group consisting of citrate or a salt thereof; ethylenediamine tetracetic acid (EDTA) or a salt thereof (for example disodium EDTA and calcium disodium EDTA); EGTA (ethylene glycol tetraacetic acid) or a salt thereof; diethylene triamine pentaacetic acid (DTPA) or a salt thereof; and BAPTA (1,2-bis(o-aminophenoxy)ethane-N,N,N',N'-tetraacetic acid) or a salt thereof. In other embodiments, one of the above-listed chelators is utilized. In more specific embodiments, the chelator is EDTA.

Oils

Those of skill in the art will appreciate, in light of the present findings, that various oils may be utilized as the basis of their liquid phase of the described compositions. In certain embodiments, the oil may be any physiologically acceptable oil that is liquid at ambient temperature.

In more specific embodiments, the oil comprises an omega-3 fatty acid. In other embodiments, the omega-3 fatty acid is an omega-3 polyunsaturated fatty acid. In another embodiment, the omega-3 fatty acid is DHA, an omega-3, polyunsaturated, 22-carbon fatty acid also referred to as 4, 7, 10, 13, 16, 19-docosahexaenoic acid. In another embodiment, the omega-3 fatty acid is—linolenic acid (9, 12, 15-octadecatrienoic acid). In another embodiment, the omega-3 fatty acid is stearidonic acid (6, 9, 12, 15-octadecatetraenoic acid). In another embodiment, the omega-3 fatty acid is eicosatrienoic acid (ETA; 11, 14, 17-eicosatrienoic acid). In another embodiment, the omega-3 fatty acid is eicosatetraenoic acid (8, 11, 14, 17-eicosatetraenoic acid). In one embodiment, the omega-3 fatty acid is eicosapentaenoic acid (EPA; 5, 8, 11, 14, 17-eicosapentaenoic acid). In another embodiment, the omega-3 fatty acid is eicosahexaenoic acid (also referred to as 5, 7, 9, 11, 14, 17-eicosahexaenoic acid). In another embodiment, the omega-3 fatty acid is docosapentaenoic acid (DPA; 7, 10, 13, 16, 19-docosapentaenoic acid). In another embodiment, the omega-3 fatty acid is tetracosahexaenoic acid (6, 9, 12, 15, 18, 21-tetracosahexaenoic acid).

In other embodiments, the oil is a naturally-occurring oil comprising an omega-3 fatty acid. In more specific embodiments, the oil is selected from the group consisting of a fish oil, canola oil, flaxseed oil, algal oil and hemp seed oil. In more specific embodiments, the oil is a fish oil. Several types of fish oil have been tested in the described compositions and have all been found to work equally well.

In other embodiments, a liquid formulation utilized in the described method or composition is water-free. "Water-free" refers, in certain embodiments, to a formulation into which no aqueous components have been intentionally added. It does not preclude the presence of trace amounts of water that have been absorbed from the atmosphere into the components thereof. In another embodiment, the liquid formulation is free of aqueous components. In yet other embodiments, one or more oils are the only liquid components of the liquid formulation. In more specific embodiments, fish oil is the only liquid component of the liquid formulation.

Coatings

Those of skill in the art will appreciate, in light of the present findings, that various pH-sensitive coatings may be utilized in the described methods and compositions. In certain embodiments, any coating that inhibits digestion of the composition in the stomach of a subject may be utilized.

In other embodiments, the coating comprises a biodegradable polysaccharide. In other embodiments, a hydrogel is utilized. In other embodiments, the coating comprises one of the following excipients: chitosan, an aquacoat ECD coating, an azo-crosslinked polymer, cellulose acetate phthalate, cellulose acetate trimellitate (CAT), cellulose acetate butyrate, hydroxypropylmethyl cellulose phthalate, or poly vinyl acetate phthalate.

In other embodiments, a timed-release system such as Pulsincap™ is utilized.

In preferred embodiments, the described coated dosage forms release the core (containing the oil-based formulation) when pH reaches the range found in the intestines, which is alkaline relative to that in the stomach. In more specific embodiments, the coating comprises a pH-sensitive polymer. In various embodiments, either mono-layer or multi-layer coatings may be utilized.

In one embodiment, the coating is an enteric coating. Methods for enteric coating are well known in the art (see, for example, Siepmann F et al 2005). In more specific embodiments, a Eudragit™ coating is utilized as the enteric coating. Eudragit™ coatings are acrylic polymers, the use of which is well known in the art.

In another embodiment, microencapsulation is used as a stomach-resistant coating in the described compositions. Methods for microencapsulation are well known in the art.

In other embodiments, the coating is a capsule, of which gelatin capsules are a more specific embodiment. Methods for inserting an oil-based formulation into a gelatin capsule are well known in the art. In still other embodiments, the coating is a soft-gel, enteric-coated capsule.

In another embodiment, an oral pharmaceutical composition is provided, comprising an oil-based liquid formulation, wherein the oil-based liquid formulation comprises a therapeutic protein of up to 100 kilodaltons, a chelator of divalent cations, an isolated chymotrypsin/trypsin inhibitor, an isolated trypsin inhibitor, and a PEG ester of a fatty acid. In other embodiments, the liquid formulation has an anti-chymotrypsin activity of at least 50 mg. chymotrypsin inhibited per ml. of the liquid formulation. In other embodiments, the liquid formulation has both an anti-chymotrypsin activity of at least 50 mg. chymotrypsin inhibited per ml. of the liquid formulation and an anti-trypsin activity of at least 25 trypsin inhibited per ml. of the liquid formulation. In other embodiments, a free PEG is also present. In other embodiments, a non-ionic detergent is also present. In other embodiments, the liquid formulation consists essentially of a therapeutic protein of up to 100 kilodaltons, a chelator of divalent cations, a chymotrypsin/trypsin inhibitor, a trypsin inhibitor, and a PEG ester of a fatty acid. In other embodiments, the liquid formulation consists essentially of a therapeutic protein of up to 100 kilodaltons, a chelator of divalent cations, a chymotrypsin/trypsin inhibitor, a trypsin inhibitor, a PEG ester of a fatty acid, and a free PEG. In other embodiments, the liquid formulation consists essentially of a therapeutic protein of up to 100 kilodaltons, a chelator of divalent cations, a chymotrypsin/trypsin inhibitor, a trypsin inhibitor, a PEG ester of a fatty acid, a free PEG, and a non-ionic detergent.

Representative Formulations

Certain representative insulin formulations comprise insulin, Gelucire 44/14, EDTA, SBTI, and aprotinin in fish oil, coated in a capsule. Certain representative exenatide formulations contain exenatide, Gelucire 44/14, EDTA, SBTI, and aprotinin in fish oil, coated in a capsule. One more specific embodiment is a formulation having the following components: 8-20% Gelucire 44/14; 50-100 mg. per capsule isolated BBI, or isolated BBI/isolated KTI mixture; 20-30 mg. per capsule Aprotinin; and 100-200 mg EDTA; with a therapeutic protein, which may be 8-32 mg. per capsule insulin and/or 150-600 mcg. per capsule Exenatide, all combined into 0.5-0.7 ml. fish oil. Another representative liquid insulin formulation contains insulin, Gelucire 44/14, EDTA, BBI, KTI, and aprotinin in fish oil. In other embodiments, the liquid formulation consists essentially of insulin, Gelucire 44/14, EDTA, BBI, KTI, aprotinin, and fish oil. More specific formulations contain 8 mg insulin, 12% Gelucire 44/14, 150 mg EDTA, 75 mg total of BBI and KTI, and 24 mg aprotinin in 0.5-0.7 ml. fish oil; 16 mg insulin, 12% Gelucire 44/14, 150 mg EDTA, 75 mg total of BBI and KTI, and 24 mg aprotinin in 0.5-0.7 ml. fish oil; and 16 mg insulin, 12% Gelucire 44/14, 150 mg EDTA, 150 mg total of BBI and KTI, and 24 mg aprotinin in 0.5-0.7 ml. fish oil. In a still more specific formulation, the ratio of the anti-trypsin activity to the anti-chymotrypsin activity of the composition is about 1.28:1. In other embodiments, the above composition further comprises a non-ionic detergent. In more specific embodiments, the non-ionic detergent is a polysorbate-based detergent. In even more specific embodiments, the polysorbate-based detergent is polysorbate 80. Preferably, the polysorbate 80 constitutes 3-10% weight/weight inclusive of the oil-based liquid formulation. The liquid formulation may be coated by a soft-gel, enteric-coated capsule. Specific formulations described in this paragraph also encompass, in certain embodiments, scaled-up and scaled-down formulation containing the same components in the same ratios.

Some representative oral exenatide formulations comprise exenatide, EDTA, BBI, KTI, and aprotinin in fish oil. In other embodiments, the liquid formulation consists essentially of exenatide, Gelucire 44/14, EDTA, BBI, KTI, aprotinin, and fish oil. More specific formulations contain 150 microgram (mcg) exenatide, 150 mg EDTA, 75 mg total of BBI and KTI, and 24 mg aprotinin in 0.5-0.7 ml. fish oil; 300 mcg exenatide, 150 mg EDTA, 75 mg total of BBI and KTI, and 24 mg aprotinin in 0.5-0.7 ml. fish oil; and 300 mcg exenatide, 150 mg EDTA, 150 mg total of BBI and KTI, and 24 mg aprotinin in 0.5-0.7 ml. fish oil. In a still more specific formulation, the ratio of the anti-trypsin activity to the anti-chymotrypsin activity of the composition is between 1.5:1 and 1:1, inclusive. In even more specific embodiments, the ratio is about 1.28:1. The liquid formulation may be coated by a soft-gel, enteric-coated capsule. In other embodiments, the above composition further comprises a non-ionic detergent. In more specific embodiments, the non-ionic detergent is a polysorbate-based detergent. In even more specific embodiments, the polysorbate-based detergent is polysorbate 80. Preferably, the polysorbate 80 constitutes 3-10% weight/weight inclusive of the oil-based liquid formulation. The liquid formulation may be coated by a soft-gel, enteric-coated capsule.

Therapeutic Indications

In another aspect is provided use of a BBI described herein in the preparation of a medicament for orally administering an active ingredient to a subject. In another aspect is provided use of a KTI3 described herein in the preparation of a medicament for orally administering an active ingredient.

In still another aspect is provided a method for making a pharmaceutical composition, comprising the steps of: (a) producing a mixture comprising a BBI described herein and an active ingredient; and (b) formulating the mixture into a pharmaceutically acceptable formulation.

In still another aspect is provided a method for making a pharmaceutical composition, comprising the steps of: (a) producing a mixture comprising a KTI3 described herein and an active ingredient; and (b) formulating the mixture into a pharmaceutically acceptable formulation.

As referred to herein, the step of formulating comprises the steps of optionally adding excipients, milling, coating, and the like, as appropriate for the desired pharmaceutical composition. These steps are well within the ability of those skilled in the art.

In certain embodiments, an active ingredient as referred to herein is sensitive to degradation or inactivation in the human digestive tract.

In another aspect is provided an oral pharmaceutical composition described herein for orally administering an active ingredient to a subject. In certain preferred embodiments, the active ingredient is sensitive to degradation or inactivation in the human digestive tract. In more specific embodiments, the active ingredient may be a therapeutic protein. In other embodiments, the active ingredient is a non-protein molecule that is sensitive to degradation or inactivation in the human digestive tract.

In another aspect is provided use of an oral pharmaceutical composition described herein in the preparation of a medicament for orally administering a therapeutic protein to a subject.

In another aspect is provided a method for orally administering a therapeutic protein to a subject, the method comprising the step of administering to a subject an oral pharmaceutical composition described herein, thereby orally administering a therapeutic protein to a subject.

In another aspect is provided a pharmaceutical composition described herein for treating diabetes in a human, where, in some embodiments, the therapeutic protein is in various embodiments insulin, exenatide, or a combination thereof.

In yet another aspect is provided a use of a combination of ingredients described herein in the preparation of a medicament for treating diabetes in a human, where, in some embodiments, the therapeutic protein is in various embodiments insulin, exenatide, or a combination thereof.

In still another aspect is provided a method for treating diabetes, the method comprising the step of administering to a subject in need of such treatment a pharmaceutical composition described herein, where, in some embodiments, the therapeutic protein is in various embodiments insulin, exenatide, or a combination thereof, thereby treating diabetes. In certain embodiments, the subject is a human subject, while in other embodiments, the subject is a non-human mammal.

In an additional aspect is provided a pharmaceutical composition described herein for treating unstable diabetes in a human. In another aspect, a pharmaceutical composition described herein is provided for treating an elevated fasting blood glucose level in a human.

In yet another aspect is provided a use of a combination of ingredients described herein in the preparation of a medicament for treating unstable diabetes in a human. Additionally, a use is provided of a combination of ingredients described herein in the preparation of a medicament for treating an elevated fasting blood glucose level in a human.

Additionally, there is provided a method for treating unstable diabetes, the method comprising the step of administering to a subject in need of such treatment a pharmaceutical composition described herein, thereby treating unstable diabetes. Further is provided a method for reducing an elevated fasting blood glucose level, the method comprising the step of administering to a subject in need of such treatment a pharmaceutical composition described herein, thereby reducing an elevated fasting blood glucose. In certain preferred embodiments, the subject is a human subject.

Unstable Diabetes

Physicians skilled in the art will appreciate that unstable diabetes, also known as glycemic lability, can be diagnosed by a number of acceptable standard procedures. One such procedure appears in Ryan et al, 2004. In this procedure, subjects are asked to monitor their glucose levels with a minimum of 2 capillary glucose readings a day. Patients record all measured glucose values and details about hypoglycemic occurrences over a 4-week period on sheets (FIG. 11A-B). On any occasion that glucose is recorded as <3.0 mmol/l, the subject is asked to describe the details of the event on the questionnaire (FIG. 12), including which symptoms occur and whether outside help from a third party is obtained to either recognize or treat the hypoglycemic reaction. A reaction is considered severe if the individual had lost control of the situation and required outside help to treat the hypoglycemic event. Other such methods involve calculation of the MAGE index (Service et al 1970) or the "M value" (Schlichtkrull et al) or utilize continuous glucose monitoring systems (Kessler et al). Unstable diabetes is typically associated with elevated fasting blood glucose and/or hypoglycemic episodes.

Methods of Isolating Protease Inhibitors

In yet another aspect is provided a method for purifying BBI from a soybean product, e.g. soy flour, comprising the steps of: a) obtaining a liquid mixture comprising an extract from the soybean product, wherein the liquid mixture is a pH-buffered aqueous solution having a pH of between 5.5-7.5 inclusive, with a salt concentration of less than 50 mM; and b). subjecting the solution to size-exclusion chromatography, utilizing a stationary phase that comprises a positively charged resin and a polysaccharide polymer material, wherein the size-exclusion chromatography comprises a discontinuous step salt gradient, wherein the salt concentration of the solution used in the first step is less than 40 mM, preferably less than 20 mM, and the salt concentration of a solution used in a subsequent step (typically but not necessarily the second step) is between 40-85 mM, more preferably 50-80 mM, more preferably 60-80 mM, more preferably 65-75 mM, most preferably 70 mM.

Alternatively or in addition, the above method further comprises the previous step of extracting soy flour at buffer with a pH of 4.5, in the presence of 80-120 mM NaCl, more preferably 100 mM NaCl, and in some embodiments subsequently adjusting the pH to 4.5, followed, alternatively or in addition, by clarification in a filter press. Alternatively or in addition, the method further comprises the previous step (before the aforementioned step of obtaining a liquid mixture having a pH of between 5.5-7.5, but subsequent to extracting the soy flour) of precipitating the initial liquid preparation of the soy flour using 30-40% saturation ammonium sulfate (AS), more preferably 35% saturation, in some embodiments under cooling, for example at a temperature of 12-17° C. In further embodiments, the precipitate is then collected by centrifugation, for example in a continuous tubular centrifuge. In still other embodiments, the AS pellet is extracted, in certain embodiments in a phosphate buffer of pH 7.0-8.0, then optionally clarified by centrifugation. In various other embodiments, the resulting supernatant is dialyzed against water, or alternatively 10 mM sodium phosphate, pH 6.0-7.0 buffer, clarified by centrifugation, and/or lyophilized.

In more specific embodiments, the above method further comprises the steps of isolating KTI by washing the column with a buffer of 90-120 mM, more preferably 100 mM, and eluting KTI with a buffer of over 150 mM, preferably 180 mM. Alternatively or in addition, the method further comprises the step of removing microorganisms through filtration (a non-limiting example is a 0.45/0.2 µm filter). Alternatively or in addition, the method further comprises the step of filtration though a 20,000-40,000 MWCO filter, preferably 30,000 MWCO, and keeping the permeate. This step is preferably done in the presence of a 0.15-0.5 M salt concentration, more preferably 0.18 M. Alternatively or in addition, the method further comprises the step of concentrating the resulting solution with a 5000 MWCO filter and keeping the retentate. Alternatively or in addition, the method further comprises the step of diafiltering the resulting solution with a 10,000 MWCO filter and keeping the retentate, for example in sodium phosphate buffer having a pH of 7.0-8.0. Alternatively or in addition, the method further comprises the step of lyophilizing the final liquid product.

In still another aspect is provided a method for purifying KTI3 (Kunitz Trypsin Inhibitor 3) from a soybean product, comprising the steps of: a). obtaining a liquid mixture comprising an extract from the soybean product, wherein the liquid mixture is a pH-buffered aqueous solution having a pH of between 6-7 inclusive, with a salt concentration of less than 50 mM; and b) subjecting the solution to size-exclusion chromatography, utilizing a stationary phase that comprises a positively charged resin and a polysaccharide polymer material, wherein the size-exclusion chromatography comprises a discontinuous step salt gradient, wherein the salt concentration of the solution used in a wash step (either the first step or a subsequent step) is more than 80 mM, and the salt concentration of a subsequent step (wherein the KTI3 is eluted) is between 140-250 mM inclusive, preferably between 160-220 mM inclusive, more preferably between 170-200 mM inclusive, more preferably 180 mM.

Alternatively or in addition, the above method further comprises the previous step of extracting soy flour at buffer with a pH of 4.5, in the presence of 80-120 mM NaCl, more preferably 100 mM NaCl. Alternatively or in addition, the method further comprises the previous step of precipitating the initial liquid preparation of the soy flour using 30-40% saturation ammonium sulfate, more preferably 35% saturation. Alternatively or in addition, the method further comprises the step of removing microorganisms through filtration (a non-limiting example is a 0.45/0.2 µm filter). Alternatively or in addition, the method further comprises the step of concentrating the resulting solution with a 5000 MWCO filter and keeping the retentate. Alternatively or in addition, the method further comprises the step of diafiltering the resulting solution with a 10,000 MWCO filter and keeping the retentate. Alternatively or in addition, the method further comprises the step of lyophilizing the final liquid product.

The "liquid mixture" referred to above may in certain embodiments be a solution, a suspension, or a combination thereof. In preferred embodiments, its salt concentration is less than 40 mM, more preferably less than 30 mM, more preferably less than 20 mM, more preferably less than 10 mM. Most preferably, no salt has been added. In other embodiments, the pH of the liquid mixture is between 6-7 inclusive.

The positively charged resin used in the above methods may be in some embodiments a diethylaminoethyl (DEAE) tertiary amine functional group. Alternatively or in addition, the polysaccharide polymer material is crosslinked through lysine side chains. One non-limiting example of such a material is Sepharose™, a crosslinked, beaded-form of a polysaccharide polymer material extracted from seaweed.

In certain embodiments, the described method of isolating protease inhibitors does not utilize a PEG-containing reagent.

Methods of Producing Pharmaceutical Compositions

Also provided herein are methods of producing pharmaceutical compositions. In certain embodiments, the method comprises the steps of optionally combining molten Gelucire (for example Gelucire 44/14) with fish oil, cooling the mixture, then adding, in powder form, EDTA, SBTI, aprotinin, and a therapeutic protein or peptide, for example insulin, or in other embodiments, exenatide, although those skilled in the art will appreciate in light of the present findings that other therapeutic proteins or peptides may be used as well. In other embodiments, the method comprises the steps of optionally combining molten Gelucire (for example Gelucire 44/14) with fish oil, cooling the mixture of, then adding, in powder form, EDTA, BBI, and a therapeutic protein or peptide. In certain embodiments, the powder components are added in the listed order. In other embodiments, the resulting mixture is optionally mixed and/or homogenized.

Wherever alternatives for single features such as purity of BBI, purity of KTI, nature of protein or nature of liquid component etc. are laid out herein as "embodiments", it is to be understood that such alternatives may be combined freely to form discrete embodiments of the entire formulation provided herein.

"Consisting essentially of", as used herein, limits the scope of the invention to the specified materials or steps and those that do not materially affect the basic and novel characteristics of the claimed invention.

With respect to the jurisdictions allowing it, all patents, patent applications, and publications mentioned herein, both supra and infra, are incorporated herein by reference.

EXPERIMENTAL DETAILS SECTION

Example 1: Small-Scale Production of Improved KTI and BBI formulations

Overview

Previous protocols for producing SBTI from soybean flour generated crude protease inhibitors at a yield of 1%. The following experiments were performed to develop a production method of separate bulk materials of KTI (Kunitz Trypsin Inhibitor) with a Trypsin inhibitor (TI) activity and BBI (Bowman-Birk Inhibitor) with a Trypsin/Chymotrypsin inhibitor (CTI) activity, where each product is prepared under its own specifications to high levels of enzymatic activity, the yield is improved, and high molecular weight (MW)-contaminants are minimized.

The production process involves two major phases:
Part 1: Production of SBTI Intermediate from Soy Flour.

Crude SBTI is precipitated from the supernatant with ammonium sulfate (AS) and collected by centrifugation. The protein is extracted and dialyzed to remove excess AS. The dialyzed extract is lyophilized, analyzed and termed the "SBTI intermediate" (FIG. 1A).

Part 2: Downstream Purification of SBTI Intermediate to Produce Purified BBI and KTI.

The SBTI intermediate is loaded on a DEAE-Sepharose™ fast flow column. KTI and BBI are separately eluted by salt step gradients. The BBI is further purified to reduce the high-MW contaminants by filtration through a 30,000 molecular weight cut-off (MWCO) filter. The final formulation is prepared in phosphate buffer before lyophilization (FIG. 1B).

Various parameters of the processes shown in FIGS. 1(A) and (B) were altered, including: the type of soy flour used as a starting material, the pH and salt level of the extraction buffer, the percentages of AS used for precipitation, the pH and salt level of the buffer used for column loading, and the elution conditions (continuous salt gradient vs. step gradient).

7B soy flour (de-fatted and minimally heat processed soy flour, produced by Archer Daniels Midland Company Decatur, Ill.) was used. The preferred pH for extraction was 4.5, which yielded a much lower level of non-relevant proteins, while keeping the level of KTI and BBI relatively high. A continuous material precipitation was observed in the absence of salt; the addition of salt to the extraction buffer improved the process considerably by preventing the precipitation. Use of 35% AS for protein precipitation resulted in a much lower level of high-MW proteins, while the level of KTI and BBI was minimally affected. Use of pH-6.5 column loading buffer reduced the amount of non-relevant proteins bound to the DEAE-Sepharose column. Elution in salt gradient steps resulted in a better separation of BBI from KTI and other non-relevant proteins. The BBI was efficiently purified by filtering through a 30,000 MWCO filter in the presence of 0.5M NaCl.

Example 2: Larger-Scale Improved SBTI Production

Three larger-scale experiments using 25 kilograms (kg) soy flour were performed. Extract collection was performed with the use of a disk stack centrifuge (Westfalia; first two experiments) or with a filter press (third experiment). 50% of the material was lost with the Westfalia centrifuge, while no loss of extract was observed with the filter press. The protocol and the analytic results of the third experiment are shown in Tables 1-2, respectively.

TABLE 1

Large-scale SBTI Intermediate preparation

| Process Step | Results |
|---|---|
| Flour extraction: Mix 25 Kg 7B flour with 250 L extraction buffer, containing 25 mM sodium phosphate and 100 mM NaCl, at pH 4.5, for one hour at room temperature, using an overhead stirrer. Adjust pH to 4.5 with concentrated HCl. | |
| Clarification: add 7.5 kg. Hyflo and filter using filter press. Wash filter press with 2 × 50 L extraction buffer. | Clear yellowish solution |
| Ammonium sulfate precipitation: 209 grams (gr)/L final concentration (=35% percent saturation). Mix | |

TABLE 1-continued

Large-scale SBTI Intermediate preparation

| Process Step | Results |
|---|---|
| 2 hours at RT, incubate overnight at 12-17° C. To 490-540 L, with a cooling coil, gradually add the AS. | |
| Precipitation of AS pellet: Collect AS precipitate by centrifugation in a continuous tubular centrifuge (Alfa Laval) at 1.8-2.2 L/min under suction. | 1.4 Kg of firm brownish pellet |
| Extraction of AS pellet: Mix pellet with 12 L of 10 mM sodium phosphate, pH 7.6 buffer for 30 min and centrifuge in a Sorvall centrifuge, keeping the supernatant. Repeat this step twice with 8 L and 4 L of buffer. | 4 cycles of extraction were required to extract all the brownish solution from the pellet. Total volume = 15 L |
| Dialysis: Pool supernatants at and dialyze in 3,500 MWCO bags against a total of 1 L water, for 40-48 hours at 4-17° C. | Beige, very hazy solution. Conductivity at the end of dialysis was 800 μSi |
| Clarification: by Sorvall centrifuge, 15 minutes at 4800 RPM. | Light brown clear suspension |
| Lyophilization: for 48-72 hours | Light brown powder, 444 gr. Final product* |

*Calculated value based on dialysis of 2.1 liter (L) aliquot.

TABLE 2

Analytical Results of SBTI intermediate.

| TEST | RESULTS |
|---|---|
| Appearance | Brown solid |
| Protein percentage by BCA | ≥102% |
| Trypsin inhibitor activity | 1 mg of protein inhibits 1.34 mg of Trypsin having an activity of approx. 10,000 BAEE units per mg. of protein |
| Chymotrypsin inhibitor activity | 1 mg should inhibit 0.98 mg of Chymotrypsin having an activity of approx. 40 BTEE units per mg. of protein |

Next, the SBTI intermediate was subjected to the downstream purification process shown in Table 3. The analytical results of the obtained KIT and BBI are shown in Tables 4-5, respectively.

TABLE 3

Large-scale downstream preparation of purified BBI and KTI.

| Step | Result |
|---|---|
| Solubilize SBTI Intermediate: 20 mg/ml. in 1250 ml. of buffer A: 10 mM sodium phosphate, pH 6.5 | Clear brownish solution, 1250 ml |
| DEAE Sepharose column chromatography: | |
| Conductivity of charge | 3.09 mS/cm |
| pH of charge | Adjust to pH 6.5 |
| Resin amount | 840 ml |
| Column size (diameter × height) | 10 cm × 10.7 cm |
| Column volume (CV) | 840 mL |
| Flow rate | 28 mL/min |
| Volume of charge | 1250 mL |
| Volume of wash | 8 L |
| Elution with buffer A containing salt as follows: 5 L (6 × CV) of 0 to 0.14M NaCl (gradient) 5 L (6 × CV) of 0.14M NaCl (step) 5 L (6 × CV) of 0.14 to 0.18M NaCl (gradient) 5 L (6 × CV) of 0.18M NaCl (step) 3 L of 0.4M NaCl (step) | Collect fractions of 0.3 L |
| Collecting BBI pool | 3.1 L clear solution |
| Collecting KTI pool | 4.5 L clear solution |
| Filtration of BBI pool (only 840 ml): Add NaCl to final concentration of 0.5M. Filter through TFF 30,000 MWCO and collect permeate | 830 ml. clear light yellow solution. Recovery by $OD_{280}$ = 61% |
| Dialysis of KTI pool and filtered BBI pool in 1000 MWCO bags against water for 2 days | Clear solutions. Conductivity of both pools is <100 uSi |
| Formulation: Add 0.5M sodium phosphate, pH 7.6 to the protein suspension so that the protein will be 90% in solid | |
| Lyophilization: in Lyoguard trays for 48 hours | *White powder of both proteins: 10.2 gr of KTI and 2.25 gr of BBI |

TABLE 4

Analytical results of purified KTI.

| TEST | ANALYTICAL RESULT |
|---|---|
| Appearance | White |
| Protein by BCA | 99% |
| Trypsin inhibitor activity | 1 mg inhibits 1.38 mg of Trypsin with activity of approx. 10,000 BAEE units per mg of protein |
| Purity by SDS-PAGE and imager Quantitation | 100% High molecular weight contaminants: <0.1%. |

TABLE 5

Analytical results of purified BBL

| TEST | ANALYTICAL RESULT |
|---|---|
| Appearance | White |
| Protein by BCA | 99% |
| Chymotrypsin inhibitor activity | 1 mg inhibits 1.49 mg. of Chymotrypsin with activity of approx. 40 BTEE units per mg of protein. |
| Purity by SDS-PAGE and imager quantitation | 89% BBI High molecular weight contaminants: <0.1%. |

Figure 2:
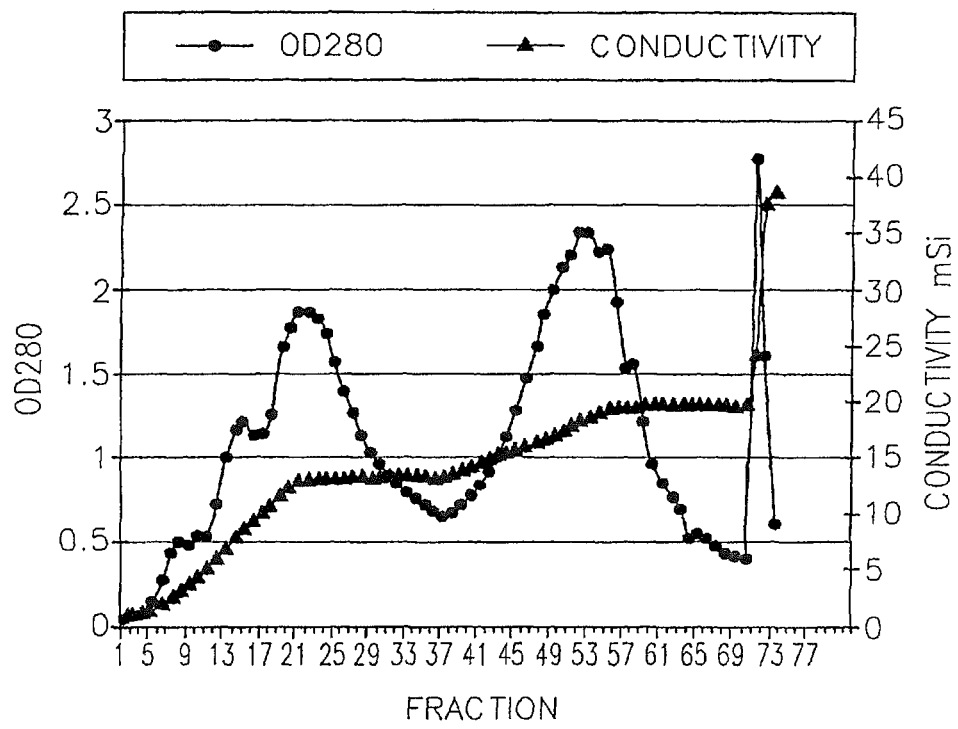
FIG. 2. Chromatogram of DEAE Sepharose™ column separation. Fractions of 0.3 L were collected during DEAE column elution.

A clear separation of the KTI and BBI fractions was achieved (FIG. 2). The elution was performed with NaCl gradient from 0 to 0.14 M, from 0.14 to 0.18 M and from 0.18 to 0.4 M. Conductivity and $OD_{280}$ were determined for each fraction. The pool of BBI was collected from fractions 18-28. The pool of KTI was collected from fractions 42-57.

Figure 3:
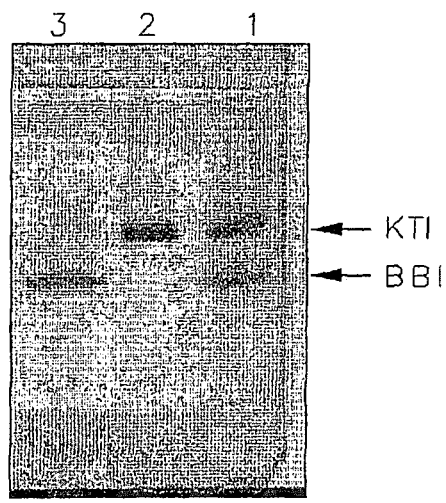
FIG. 3. SDS-PAGE analysis of purified BBI and KTI. Electrophoresis was performed, the gel was scanned, and bands were quantified using an ImageScanner™ III in conjunction with ImageQuant™ TL (both from General Electric). Samples of 1 milligram per milliliter (mg./ml.) were loaded on a 20% Phastgel™. Lane 1: Control (old SBTI preparation). Lane 2: Purified KTI, Band quantity=100%. Lane 3: Purified BBI, lower band quantity=89.2%, upper band quantity=10.8%.

The products of each pool were analyzed by SDS-PAGE. A high-purity product was obtained in each case (FIG. 3).

Thus, significant improvements in the synthetic method and the resulting product were achieved.

TABLE 6

A summary of the characteristics of the different preparations.

| Step | Previous procedure | Small-scale prep | Large-scale prep |
|---|---|---|---|
| SBTI intermediate preparation | | | |
| Starting material (flour) | 1,013 Kg | 0.2 Kg | 25 Kg |
| Clarification of flour extraction | — | 7.84 gr protein (3.92%) | 1,862 gr (7.5%) |
| SBTI intermediate | 10 kg | 3.5 gr | 444 gr |
| Protein yield | 0.98% | 1.75% | 1.78% |
| Downstream SBTI purification | | | |
| Protein Loaded on column | 2,000 gr | 3.5 gr | 30 gr |
| Final product (BBI + KTI) | | 0.449 | 2.31 grBBI 10.35 gr KTI |
| Purification yield | 6.2% for BBI and 61% for KTI | 13-17% of a mixture of both proteins | 7.4% of BBI and 34% of KTI |
| Degree of BBI purification | + | +++ | +++ |
| BBI Activity | 1.2 | 0.03-0.3 | 1.49 |
| KTI activity | 1.29 | 1.5-1.8 | 1.34 |

Example 3: Alternative Downstream BBI and KTI Purification Protocol

Description of Changes

Several changes were made to the downstream purification protocol:

1. Addition of Thimerosol to the Pools Collected from the Columns.

The BBI lots prepared without thimerosal were found to contain a high total aerobic microbial count (CFU/G) that was above the bio-burden specification of ≤100 CFU/G. The total aerobic microbial count results (CFU/G) were: KTI, Lot 1: 0; BBI, Lot 2: 15.4; BBI, Lot 3: 61.6; BBI, Lot 4: 15.4. Therefore, thimerosal was added to the pools that were collected from the column to a 0.01% final concentration. All the subsequent lots were found to be within the bio-burden specification. The total yeast and mold counts were zero for all lots.

2. Improved Salt Gradients.

In order to better separate the BBI from KTI, a stepwise salt gradient was performed, using pre-prepared buffers with known conductivity.

3. Improved Filtration Process

The 30,000 MWCO filtration process was adapted to use the KVICK™ holder outside the system instead of the Uniflux10™ system. The use of the KVICK holder enabled cycling of the material through the filters and handling large volumes at a time. The filtration was performed in a contained fashion, to the extent possible.

This change was found to minimize loss of protein and BBI activity. Prior to the change, 40-70 gram of final product with a BBI activity of 0.4-0.6/mg was obtained per purification lot. Afterwards, 85-135 gram of final product with a BBI activity of 0.8-1.4/mg was obtained. Also, the solution used for the ultrafiltration was changed from 0.5 M NaCl to 0.18 M NaCl.

Detailed Protocol

The downstream purification was performed in a cGMP facility, starting with 800 gr and 350 gr batches of SBTI intermediate. The intermediate was suspended with 40 L buffer A and loaded on the DEAE column (37 L=CV). The quality control (QC) results for the loaded material were 31.47 mgP/ml; KTI: 0.97; BBI: 0.09. The column was washed sequentially with:

1) 4×CV buffer A (10 mM sodium phosphate pH 6.5, 1.5 mSi (milliSiemens per meter);
2) 2.1×CV buffer A1 (10 mM sodium phosphate pH 6.5+75 mM NaCl, 9.9 mSi);
3) 3×CV buffer A2 (10 mM sodium phosphate pH 6.5+100 mM NaCl, 12 mSi); and
4) 4×CV buffer A3 (10 mM sodium phosphate pH 6.5+180 mM NaCl, 21 mSi).

The BBI pool consisted of fractions F5-F11 and had a volume of 130 L and 1.46 mgP/ml. The KTI pool consisted of fractions F15-F18 and had a volume of 85 L. Thimerosal was added to both pools to final concentration of 0.01%. Stock NaCl solution was added to the BBI pool to a final concentration of 0.5 M NaCl.

Next, the BBI pool was subjected to filtration, using the Kvick holder, with five 30,000 MWCO cassettes. The permeate was retained. The KTI pool was concentrated 5-fold by the Uniflux system with 3 cassettes of 10,000 MWCO to a final volume of 17.5 L. The concentrated pool was diafiltrated against water by the Uniflux10 system with 3 10,000 MWCO cassettes.

Figure 4:
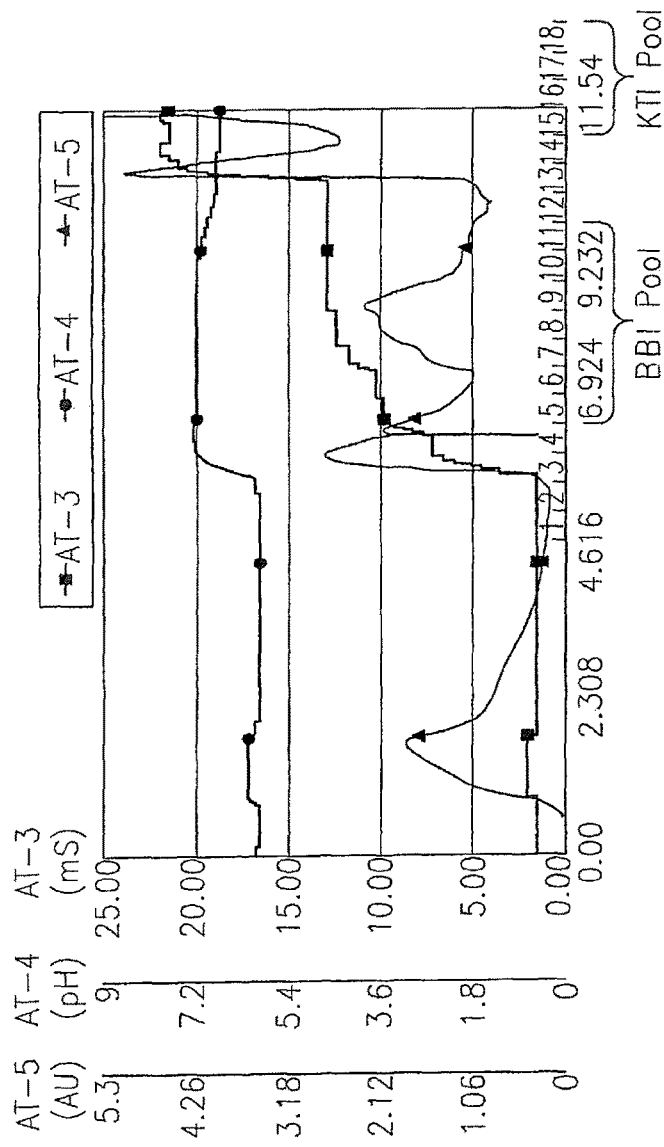
FIG. 4. Small-scale column chromatography run report using improved procedure. Squares, circles, and triangles denote conductivity plot, pH, and $OD_{280}$, respectively. Vertical axes: conductivity plot (milliSiemens), pH, and $OD_{280}$ (arbitrary units). Horizontal axis: column volume and fraction number.
Figure 5A:
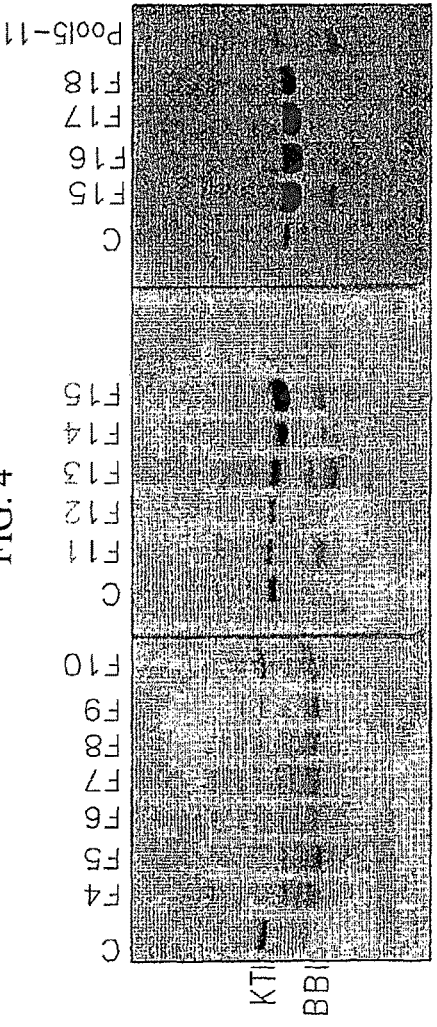
FIG. 5(A): Left-to-right presentation of fractions 4-18 and pooled fractions 5-11. "C" denotes prior art trypsin inhibitor (Sigma-Aldrich cat. no. T9003).
Figures 5B, 5C:
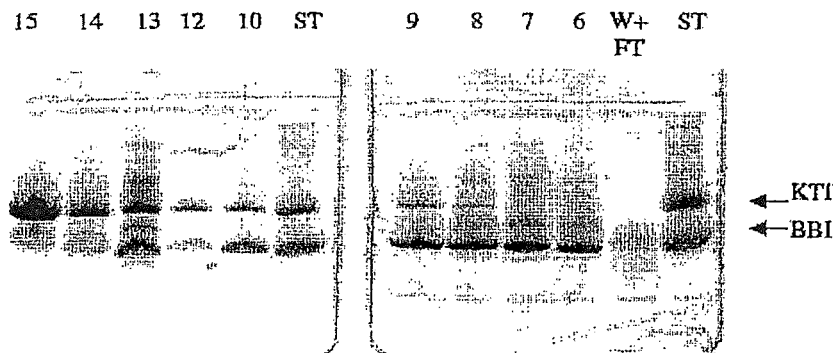
FIGS. 5B AND 5C: Right-to-left presentation of fractions 6-15, including the wash+flowthrough (W+FT) and standard (Trypsin inhibitor from *Glycine max* (soybean); "ST").

To test the efficacy of the above protocol, small-scale column chromatography was performed, and the different fractions were tested, yielding the improved results shown in FIGS. 4-5, respectively. These results were found to be reproducible over several runs.

Figure 6:
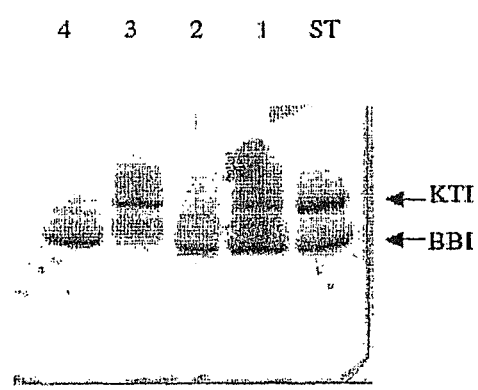
FIG. 6. SDS-PAGE analysis of steps of additional purification of BBI only. ST=standard (see FIG. 5(A-C) legend), 2 mg/ml. Lanes: 1: BBI pool from column. 2: Permeate of 30 KDa filtration. 3: Retentate of 30 KDa filtration diluted 1:40. 4: Retentate of 5 KDa concentration diluted 1:4.
Figure 7:
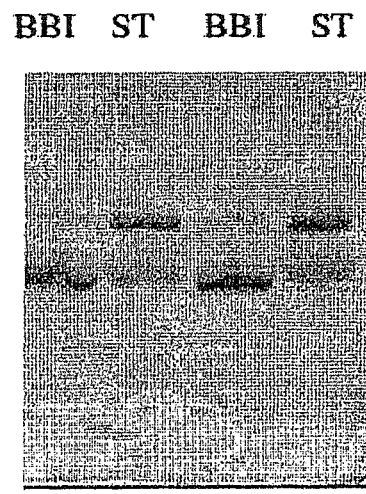
FIG. 7. SDS-PAGE analysis of 1 mg/ml. of the final product of purification of BBI only. ST=standard (see FIG. 5 legend), 1 mg/ml.

A similar protocol was repeated to purify BBI only, except that 3.5× buffer A having 12.4 mSi was utilized, and the buffer A3 elution was not performed. Additionally, after ultrafiltrating the BBI pool (135 L) with 2 KVICK holders, using 30,000 MWCO filters (2×0.55 m$^2$), the permeate was then concentrated 4.5 times, using the same system but with 5,000 MWCO filters. The concentrated retentate was diafiltrated against water in the Uniflux system. Samples of each purification step and the final product were tested by SDS-PAGE, according to the protocol below; results are shown in FIGS. 6 and 7, respectively.

The SDS-PAGE utilized ready-to-use gels (PhastGels™, 20%, from Amersham Pharmacia) run in a Phast™ system (Pharmacia). The staining solution was 50% methanol, 10% acetic acid, and 0.05% Brilliant Blue. The de-staining solution was 30% methanol, 10% acetic acid.

A sample from each step was analyzed for protein concentration and BBI activity. The results are summarized in Table 7. For the final product, the quantified imaging showed 84.4%-84.9% for the BBI band.

TABLE 7

Yield of protein and activity during the BBI purification steps.

| Step | BCA (mgP/ml) | Volume (L) | Total protein (gr) (%) | BBI activity (mg ChymoTrypsin inhibited/1 mgP-ChymoTrypsin Inhibitor) | Total BBI activity, units (%) |
|---|---|---|---|---|---|
| Column Load | | 40 | 1,100 | | |
| BBI pool | 2.1 | 135 | 283 (25.7%) | 0.5 | 141,500 |
| BBI permeate of 30 Kda. | 0.84 | 173 | 145 (13%) | 0.8 | 116,000 (82%) |
| Retentate of 30 KDa | 41.6 | 2.5 | 104 (9.45%) | 0.13 | 13,500 (9.5%) |
| Retentate of 5 KDa after 4.5 × concentration. | 3.84 | 36 | 138.24 (12.5%) | 0.8 | 110,600 (78%) |
| Permeate of 5 KDa | 0.12 | 120 | 14.4 | 0.13 | 1,872 |
| Retentate of 10 Kda after diafiltration | 4.03 | 36 | 145 (13%) | 0.7 | 101,500 (71%) |
| Final after lyophilization "as-is" | 1.07 mgP/mgS | 136 gr solid | 136 gr solid (12.3%) | 0.8/mg solid* | 108,800 (77%) |

*The material contains 10% water, therefore the result of activity is 0.9 on the basis of dry weight.

Figure 8:
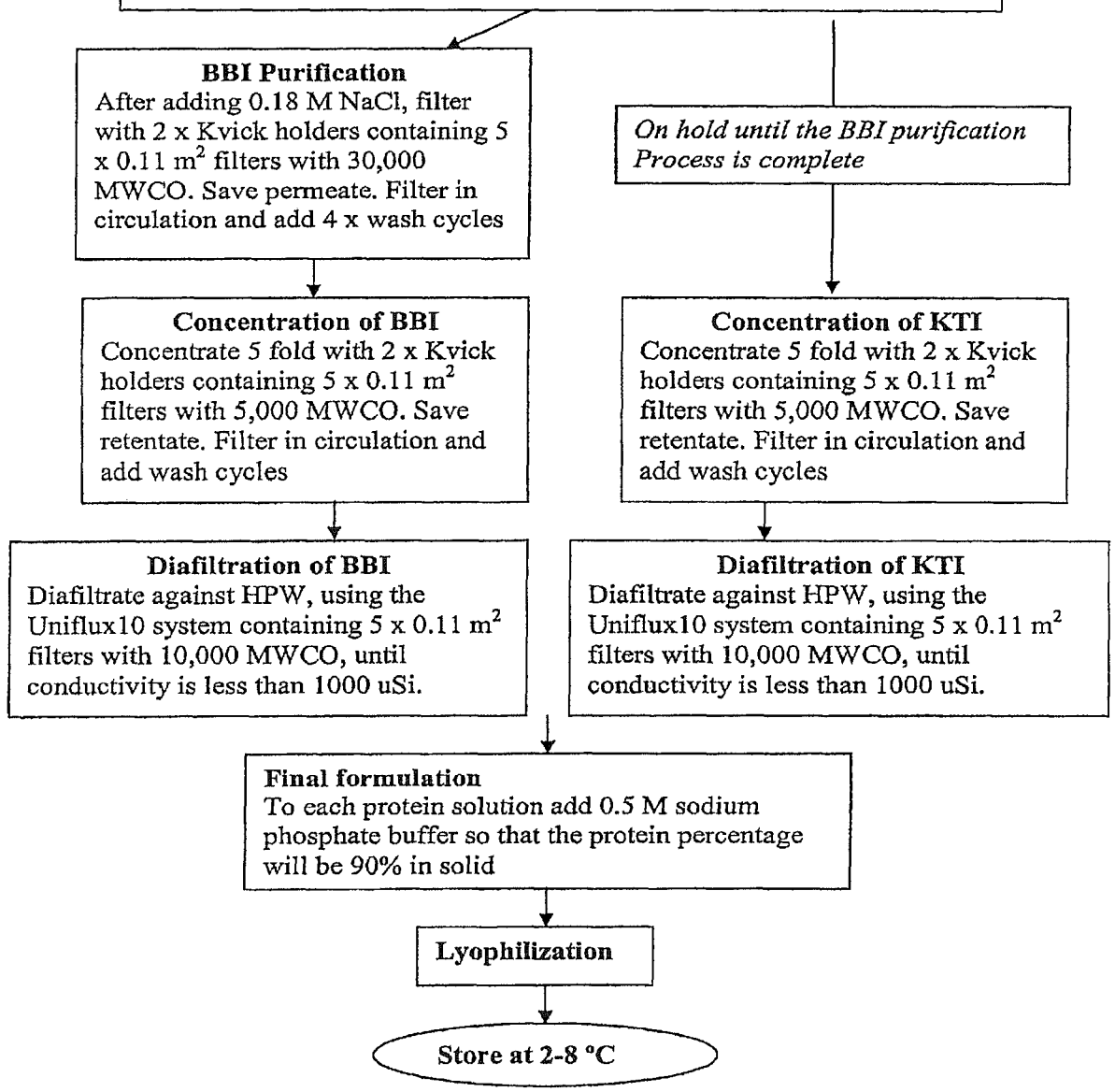
FIG. 8. Flowchart of revised protocol for downstream purification of BBI and KTI.

A flow chart of the improved protocol is shown in FIG. 8.

Prior to the improvements described in Examples 1-3, large-scale SBTI purifications yielded 40-70 gram of final product per purification lot, with a BBI activity of 0.4-0.6/mg (while somewhat higher activity was obtained in smaller-scale preparations, this could not be successfully scaled-up). The changes enabled a yield of 85-135 gram of final product with a BBI activity of 0.8-1.4/mg.

Example 4: Downstream BBI and KTI Purification Protocol Using Microfiltration

The protocol in this Example was performed without thimerosal. Starting with the SBTI intermediate, DEAE column chromatography was performed similarly to the last Example but with slightly different parameters, as follows:

3×CV buffer A (10 mM sodium phosphate pH 6.5, 1.5 mSi)
2.1×CV buffer A1 (10 mM sodium phosphate pH 6.5+70 mM NaCl, 9.9 mSi)
3.5×CV buffer A2 (10 mM sodium phosphate pH 6.5+100 mM NaCl, 12.4 mSi)
3.5×CV buffer A3 (10 mM sodium phosphate pH 6.5+180 mM NaCl, 21 mSi)

Figure 9:
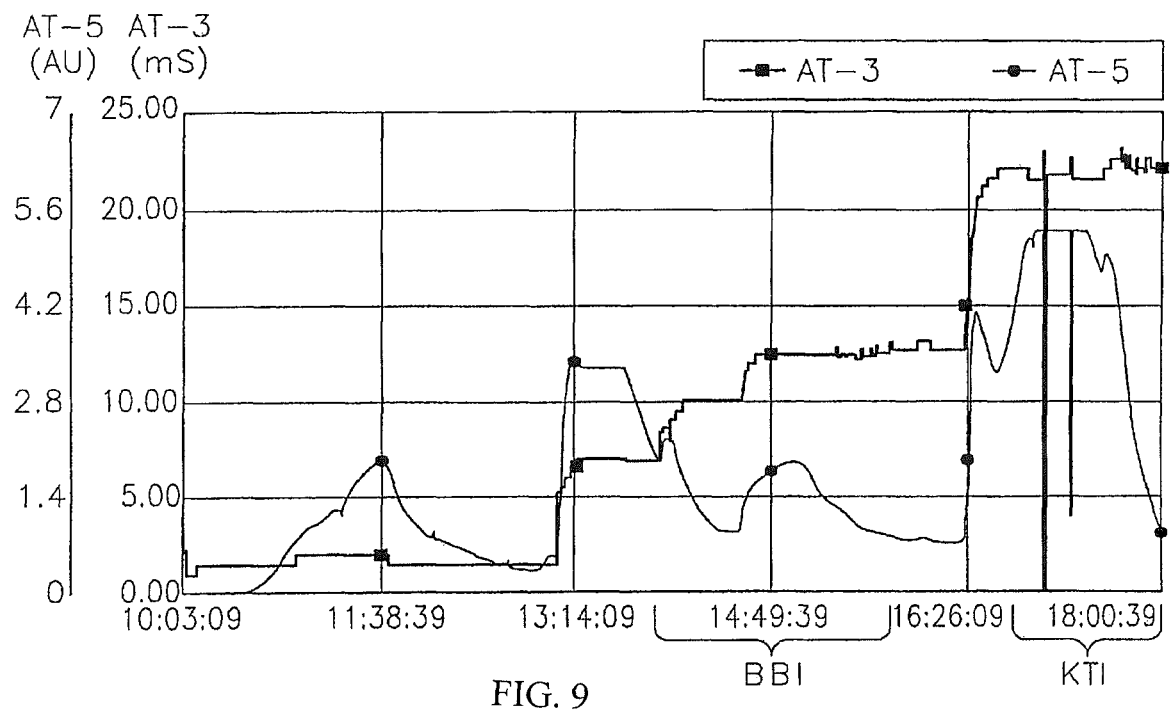
FIG. 9. Column chromatography run report using alternative procedure.

Results are shown in FIG. 9.

BBI Pool

The BBI pool, 130 L, was collected and filtered through a Sartobran™ 0.45/0.2 µm filter (0.6 m²).

KTI Pool

The KTI, 95 L, was collected and filtered through a Sartobran™ 0.45/0.2 µm filter (0.6 m²) and stored at −20° C. Final volume=20 L.

BBI Purification 30,000 MWCO Filtration

The BBI pool was adjusted to 0.18 M NaCl concentration and subjected to filtration using 2× Kvick™ holders, each with 5 cassettes of 30,000 MWCO. The permeate, after four washes, was collected, 195 L total Concentration The permeate of the 30,000 MWCO was concentrated 5 times through 2 KVICK holders, each with five 5,000 MWCO cassettes in each. Final volume=34 L.

Diafiltration

The concentrated material was diafiltrated against purified water using a Uniflux10 system with 5×10,000 MWCO filters to a conductivity of less than 1 mSi/cm.

Formulation buffer (0.5 M sodium phosphate buffer, pH 7.6) was added, and the sample was passed through a 0.45/0.2 µm filter directly into Gore® Lyoguard® Freeze-Drying Trays.

Lyophilization

After lyophilization, 95 gr. of dry material was obtained and collected into glass amber bottles.

All bottles were QC sampled: The water content was found to be 8% by the Karl Fischer method.

Figure 10:
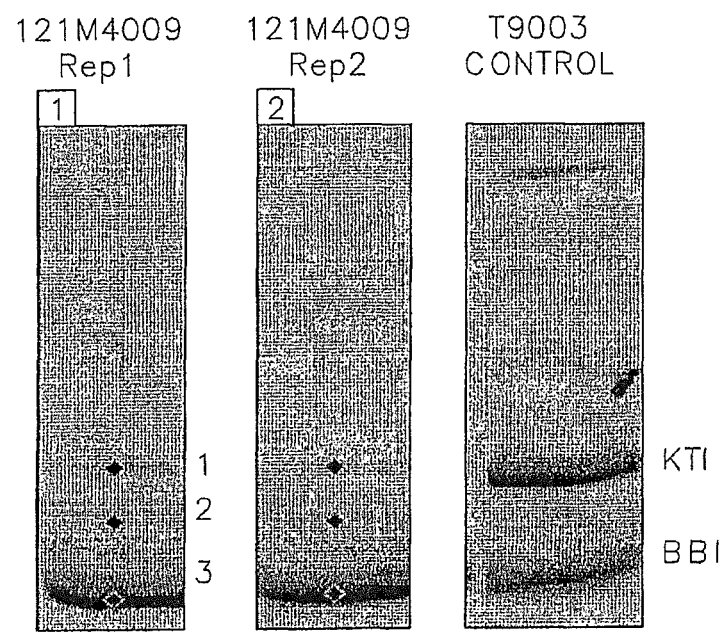
FIG. 10. SDS-PAGE analysis of duplicate samples of BBI purified using alternative procedure (lanes 1-2) vs. standards (lane 3).

Two duplicate samples were tested by SDS-PAGE, and the gel was quantified using an imager. The BBI in both lanes was at 93.5-93.8% purity (FIG. 10).

Samples from each BBI purification step were tested for protein concentration, BBI activity and bio-burden. Table 8 summarizes the BBI quantity and quality along the purification process:

TABLE 8

BBI purification steps, quantity, characteristics, and bio-burden.

| Step | BCA (mgP/ml) | Volume (L) | Total protein (gr) | BBI (mg ChymoTrypsin inhibited/1 mgP-ChymoTrypsin Inhibitor) | Total BBI activity | Bio-burden (TAMC) (CFU/ml) |
|---|---|---|---|---|---|---|
| Column Load | NA | 46 | 1,100 | NA | NA | TNTC |
| BBI pool | 1.4 | 130 | 182 | 0.6 | 109,000 | TNTC |
| BBI pool after microfiltration 0.45/0.2 | 1.4 | 130 | 182 | 0.6 | 109,000 | 1 |
| BBI permeate, after 30 Kda UF and additional washes | 0.7 | 195 | 136.5 | 0.8 | 109,000 | 10 |
| Retentate of 5 KDa after 5x concentration | 3.6 | 34 | 122.5 | 0.9 | 110,250 | 148 |
| Retentate of 10 Kda after diafiltration | 3.1 | 34 | 105 | 1.0 | 105,000 | TNTC |
| BBI After formulation and microfiltration 0.45/0.2 | 3.0 | 34 | 102 | 0.8 | 81,600 | 0 |
| Final after lyophilization | — | — | 95 gr solid | 0.9 | 85,500 | 0 |

TNTC = too numerous to count

KTI Purification

Concentration of KTI

The microfiltrated KTI pool was taken out of cold storage and concentrated using 2×KVICK holders with 5 5 KDa MWCO filters each. Final volume=17 L Samples from each KTI purification step were tested for protein concentration, KTI activity and bio-burden. Table 9 summarizes the KTI quantity and quality along the purification process:

TABLE 9

KTI purification steps, quantity, characteristics, and bio-burden.

| Step | BCA (mgP/ml) | Volume (L) | Total protein (gr) | KTI (mg Trypsin inhibited/1 mgP-Trypsin Inhibitor) | Total KTI activity | Bio-burden (TAMC) (CFU/ml) |
|---|---|---|---|---|---|---|
| Column Load | NA | 46 | 1,100 | NA | NA | TNTC |
| KTI pool | 4.5 | 95 | 427.5 | 1.5 | 641,250 | TNTC |
| KTI pool after microfiltration 0.45/0.2 | 4.3 | 95 | 408.5 | 1.5 | 612,750 | TNTC |
| Retentate of 5 KDa after 5x concentration | 24.7 | 17 | 419.9 | 1.3 | 545,870 | $4.2 \times 10^7$/ml |
| Retentate of 10 Kda after diafiltration | 18 | 20 | 360 | 1.5 | 540,000 | $3.4 \times 10^7$/ml |
| KTI After formulation and microfiltration 0.45/0.2 | 18 | 20 | 360 | 1.4 | 504,000 | 0.0 |
| Final after lyophilization | — | — | 300 gr solid | Not yet | | Not yet |

Diafiltration of KTI

The concentrated material was diafiltrated against water by Uniflux with 5×10,000 MWCO filters. Final volume=20 L Formulation buffer was added, and the sample was passed through a 0.45/0.2 μm filter directly into Gore lyophilization trays.

Lyophilization

The lyophilized product was removed and transferred to 4 amber glass bottles.

Conclusions

1. The SBTI intermediate has a relatively high bio-burden, which can be removed by the second microfiltration.

2. The final products following microfiltration are within the required specifications.

3. The use of microfiltration has no significant effect on the yield or specific activity of BBI and KTI.

Example 5: Identification of Effective Emulsifiers for Homogenous Insulin/Fish Oil Preparations Previous formulations of insulin in fish oil were found to slowly precipitate; they were thus unsuitable for large-scale pharmaceutical dosage form preparation. New formulations containing 3.375 g. SBTI per 22.5 g. of fish oil and containing the following emulsifiers were tested: lecithin (trial sequence 1), Polysorbate 80 (Tween-80) (sequence 2), or Gelucire 44/14 (sequence 3), alone or in combination with each other or glycerol monostearate (GMS) (FIG. 11). Subsequently, the most promising formulations (indicated with an asterisk) were produced again by melting the Gelucire (which was a waxy solid as ambient temperature), then adding it to the fish oil. After cooling this mixture, the solid components were added in powder form in the following order: EDTA, SBTI, aprotinin, and insulin; and the resulting liquid was mixed and homogenized on a roller mill.

Example 6: In Vivo Animal Testing of Various Emulsifier Formulations

Materials and Experimental Methods
Formulations
The formulations that were tested are shown below in Table 10. The percentages of emulsifiers given are weight/weight with respect to weight of the liquids present.

TABLE 10

Formulations used in this Example.

| Formulation name | Emulsifiers | Other ingredients |
|---|---|---|
| Experiment 6A | | |
| GMS 2% | GMS 2% only | 75 mg SBTI, 150 mg EDTA, 24 mg aprotinin, 8 mg human insulin, 0.5-0.7 ml of fish oil |
| 2%-2% | 2% GMS, 2% lecithin | Same as above. |
| 2%-10% | 2% GMS, 10% lecithin | Same as above. |
| 10% lec. | 10% lecithin only | Same as above. |
| Experiment 6B | | |
| A | 5% lecithin, 2% GMS | Same as above. |
| B | 3% lecithin, 12% Gelucire 44/14 | Same as above. |
| C | 6% lecithin, 12% Gelucire 44/14 | Same as above. |
| D | 5% Tween-80, 12% Gelucire 44/14 | Same as above. |
| E | 10% Tween-80, 12% Gelucire 44/14 | Same as above. |
| F | 12% Gelucire 44/14 only | Same as above. |

Husbandry

Animals: Only healthy pigs, as certified by a clinical veterinarian, were used for the study.

Housing: Solitary when with CVC and grouped at other times. Bedding: Concrete+woodchips. Illumination: 12-12 h light cycle. Temperature: 19-25° C.

Identification

Each animal was uniquely identified via ear tags.

Experimental Design

Animals were deprived of food 24-36 hours prior to testing and during the ensuing monitoring period. Access to water was ad libitum.

Animals were anesthetized with 20 mg/kg ketamine+2 mg/kg xylazine. Fasting and anesthetized pigs were positioned on their left side before liquid formulations were administered under endoscopic guidance, directly to the duodenum. After injection of the formulation, 1 ml. fish oil was injected, followed by 10 ml. air, to flush the apparatus, thereby ensuring administration of all materials. Pigs were then returned to their pens to allow for full recovery from the anesthetic treatment, which required 10-15 min. Blood samples (0.5 ml. of which were tested) were periodically drawn from the central line catheter (CVC) over the ensuing 240-min monitoring period. Blood glucose concentrations were determined from each sample, at each time point. Piglets were intravenously treated with gentamycin (100 mg/10 kg) after every experiment day to avoid infection. In cases where glucose concentrations dropped below 30 mg/dL, piglets were served commercial pig chow, and glucose concentrations were monitored for an additional 30 minutes thereafter.

A washout period of at least 2 days was enforced between test days.

Results 10 insulin-fish oil formulations with different emulsifiers were tested for in-vivo activity on blood glucose levels in 2 separate experiments. Results are shown in Table 11.

TABLE 11

Results of Experiment 6A. The three numbers in each box indicate baseline value, lowest value, and end (20 mg/dL). "Low" indicates a value of less than 20 mg/dL.

| Formulation | Pig 1 | Pig2 | Pig3 | Pig4 | Pig 5 (stoma) | Score* |
|---|---|---|---|---|---|---|
| GMS 2% | 78 → 48 → 65 | 72 → low → low | 63 → 23 → 28 | 67 → 32 → 60 | 55 → 21 → 58 | 3 |
| 2%-2% | 82 → Low → 65 | 78 → 45 → 76 | 85 → 30 → 68 | 78 → 23 → 61 | | 2 |
| 2%-10% | 76 → Low → 77 | 76 → low → 21 | 76 → low → low | 74 → low → 70 | | 4 |
| 10% lec. | 51 → 63 → 71 | 50 → low → low | 57 → low → low | 61 → low → low | | 5 |

TABLE 11-continued

Results of Experiment 6A. The three numbers in each box indicate baseline value, lowest value, and end (20 mg/dL). "Low" indicates a value of less than 20 mg/dL.

| Formulation | Pig 1 | Pig2 | Pig3 | Pig4 | Pig 5 (stoma) | Score* |
|---|---|---|---|---|---|---|

*see FIG. 11 legend.

Figures 2, 12B:
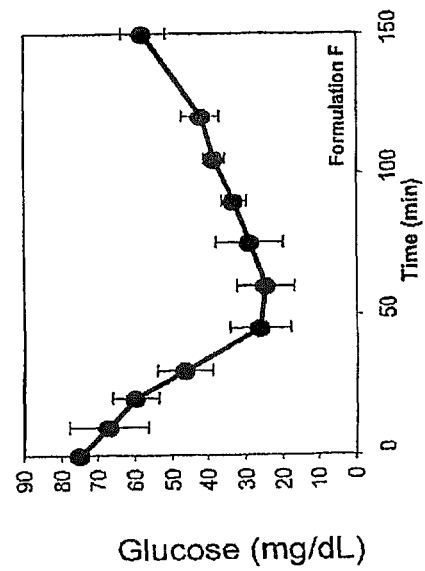
Figures 1, 12B:
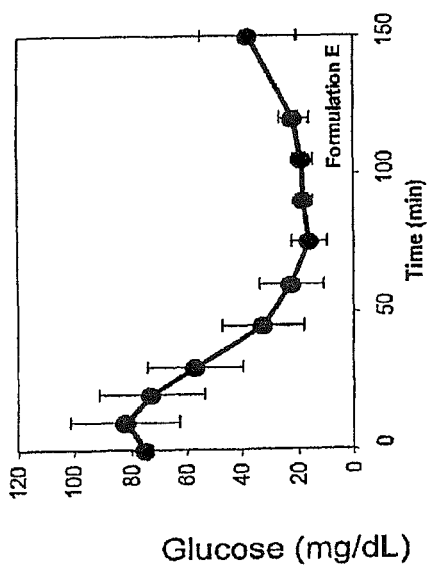

The results of Experiment 6B, depicted in FIG. 12(A)-1 to FIG. 12(A)-4; FIGS. (12B)-1 and 12(B)-2, show that while all the formulations were efficacious, formulations E and F from Table 10 induced the most uniformly sharp drops in glucose levels.

Example 7: Clinical Testing of Oral Protein Formulations Containing Improved SBTI A study was performed to determine the safety, pharmacokinetics, and pharmacodynamics of the described oral insulin formulations in healthy volunteers. Subjects received a single dose of one of the following oral insulin tablet formulations on separate visits. Each dose was followed by a 72-hour washout period. Doses were administered in the morning after an 8-hour overnight fast.

Treatment Groups
1. 1 capsule of 8-mg Insulin Formulation: 8 mg Insulin, 150 mg EDTA, 75 mg total of a mixture of purified BBI and purified KTI, 150000 U Aprotinin, and 12% Gelucire 44/14.
2. 1 capsule of 16-mg Insulin Formulation: 16 mg Insulin, 150 mg EDTA, 75 mg total of a mixture of purified BBI and purified KTI, 150000 U recombinant Aprotinin and 12% Gelucire 44/14.
3. 2 capsules of 8-mg Insulin Formulation.

Screening Phase:
The following evaluations were performed after the subject signed informed consent:
Medical history
Physical examination
Medication history
ECG
Vital signs (blood pressure, heart rate). Vital signs were measured in the sitting position after at least 5 minutes of rest.
Clinical laboratory evaluations (chemistry, hematology)
Treatment Phase
Subjects entered the clinic on the morning of dosing after an 8-hour overnight fast.
Prior to study drug administration:
An indwelling catheter was inserted for blood sample collection.
A glucose test (one drop) was performed 15 minutes (min) prior to study drug administration
Vital signs were recorded 20 min prior to study drug administration. Vital signs were measured in the sitting position after at least 5 min of rest.
Blood samples for insulin, plasma glucose and c-peptide analysis were collected 15 min prior to study drug administration.
Protocol for Drug Administration:
The experimental drug was administered orally with at least 300 mL of water. Subjects remained in an upright or sitting position for at least one hour after taking study medication.
Vital signs (blood pressure, heart rate) were recorded at approximately 2 and 5 hours (hr) post study drug administration. Vital signs were measured in the sitting position after at least 5 min of rest.
Blood samples for insulin, plasma glucose, and c-peptide analysis were collected every 20 min during the first hr. and then every 15 min up to 5.0 hr post study drug administration.

Figure 15:
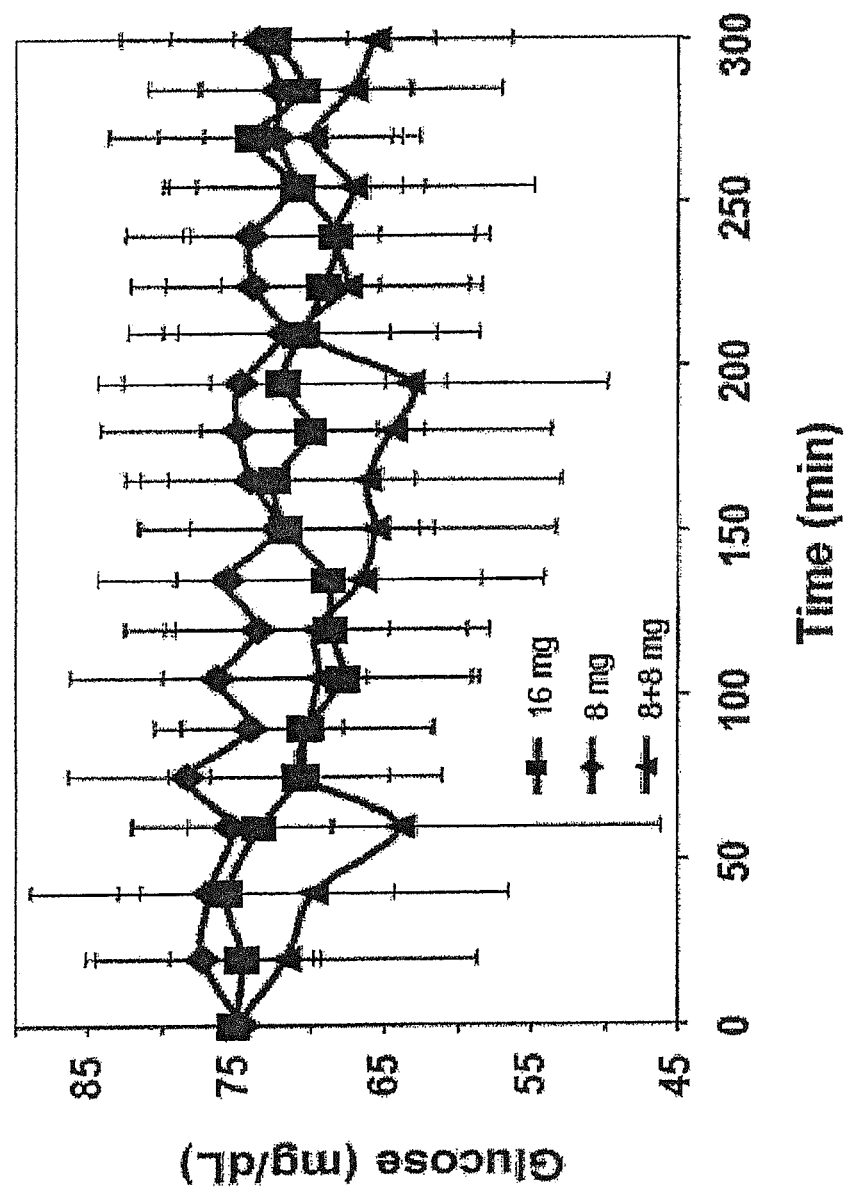
FIG. 15. Glucose responses in subjects treated with various doses of oral insulin.

After completing the evaluations for each period, the subjects were fed and discharged, then asked to return for the next period after a minimum of 72-hour washout period.
End of Study/Early Discontinuation:
Prior to discharge from the research unit, subjects underwent the following end-of-study evaluations:
Vital signs were measured in the sitting position after at least 5 min of rest.
Clinical laboratory evaluations (hematology, chemistry)
Subjects that discontinued early completed the end-of-study evaluations at the time of discontinuation.
Results
The various doses of insulin were well tolerated, with no adverse events reported or observed following any of the treatments. Responses were demonstrated in 7/10 subjects, with maximal blood glucose responses for all treatments observed following a lag of ≥60 min from administration. Significantly lower mean blood glucose $C_{min}$ was observed following the 8+8 mg (47.9±11.3 mg/dL, p=0.006) and 16 mg (57.3±8.4 mg/dL, p=0.001) treatments, when compared to the 8-mg group (64.6±6.2 mg/dL). Significant reductions in glucose area under the curve (AUC) values were observed following both 8+8 mg and 16 mg treatments (13.2% and 8.1%, respectively), when compared to 8 mg (p=0.003 and 0.008, respectively) (FIG. 15 and Table below). Such differences were not seen with formulations containing prior art SBTI preparations.
Summary of Area-Under-The-Curve (AUC) Data Following Insulin Administration

| Treatment | Avg AUC (mg/dL*min) | St-dev (mg/dL*min) |
|---|---|---|
| 8 | 22425 | 2153 |
| 16 | 20610 | 1428 |
| 8 + 8 | 19471 | 2126 |

Example 8: Animal Testing of Oral Protein Formulations Containing Improved SBTI Additional animal testing is performed on formulations comprising highly purified SBTI and a protein drug (e.g. insulin or exenatide), in a manner similar to one or more of the protocols described herein. In some experiments, liquid formulations are coated with a gelatin and/or enteric-coated capsule, which may be administered orally. In other experiments, liquid formulations are administered directly to the duodenum via a cannula or the like. In certain experiments, animals are allowed to eat prior to or following administration of the formulation, to simulate pre-prandial or post-prandial conditions.

In still other experiments, recombinant SBTI is used as described above. In other experiments, synthetic SBTI is used as described above.

Example 9: Testing of Oral Exenatide Formulations Containing Improved SBTI in Human Subjects The following study is being performed to assess the safety, pharmacokinetics and pharmacodynamics of oral exenatide formulations comprising purified BBI and KTI and optionally 12% Gelucire 44/14 in healthy volunteers and in T2D subjects, with screening and treatment performed similarly to Example 7:

Stage I:

Stage I consists of two segments: Segment 1 will assess the safety, tolerability and the PK/PD of escalating doses of oral exenatide in healthy volunteers. In the first segment, the two lower doses of exenatide (150 and 300 μg) will be randomly administered to all healthy, fasting subjects. If deemed safe, further dose escalation (450 and 600 μg exenatide) will be authorized in Segment 2. The highest tolerable dose will then be administered to all healthy patients 60 minutes before a standard meal (Visit 5).

Stage II:

This stage will assess the T2DM patient response to escalating doses of exenatide when delivered 60 min before a standard meal. Placebo controls may be included in the study, as may treatment with an active control of Byetta (5 μg) subcutaneously delivered 30 min before a standard meal. In addition, all T2DM subjects will be treated with an oral insulin capsule containing 16 mg of insulin and with a combination of oral insulin/oral exenatide, at two independent study visits, 60 minutes before being served a standard meal.

Interpretation:

AUC of glucose reductions and insulin excursion will be calculated and compared between the different treatments. The efficacy of the formulation will be shown by insulin excursions in the oral GLP-1-treated group that are greater than those in the non-GLP-1-treated group, and/or smaller glucose excursions in the oral GLP-1-treated group.

In still other experiments, recombinant BBI (optionally with KTI and/or aprotinin) is used as described above in place of purified BBI and KTI. In other experiments, synthetic BBI (optionally with KTI and/or aprotinin) is used as described above in place of purified BBI and KTI.

Example 10: Testing of Oral Insulin Formulations Containing Improved SBTI in Human Subjects The following study is being performed to assess safety and pharmacodynamics of multiple bedtime doses of oral insulin formulations comprising purified BBI and KTI and optionally 12% Gelucire 44/14, in adult patients with T2DM who are inadequately controlled with diet and metformin, with screening and treatment performed similarly to Example 7:

Primary Objectives:

To evaluate the pharmacodynamic effects of the formulation on mean nighttime glucose levels and safety parameters (e.g., hypoglycemia), and to evaluate safety, including incidence of hypoglycemia and cardiovascular events. Primary efficacy endpoints will be determined by:

The effect of 24 mg insulin on weighted mean nighttime glucose levels based on two nights of (continuous glucose monitoring (CGM)) data*, determined by comparison of:

a) The mean percent change between baseline (run-in period) and 24 mg insulin treatment to
b) The mean percent change between baseline and placebo treatment for the group receiving placebo.

* "CGM data" as used herein is always based entirely on data collected within the first six hours after oral medicinal treatment.

The effect of 16 mg insulin on weighted mean nighttime glucose levels based on two nights of CGM data determined by comparison of:

a) The mean percent change between baseline (run-in period) and 16 mg insulin treatment to
b) The mean percent change between baseline and Week 4 of placebo treatment for the group receiving placebo.

Secondary Objectives:

To evaluate changes in baseline in fasting blood glucose (FBG), morning fasting serum insulin, c-peptide, triglycerides, and HbA1c. Secondary endpoints will be determined by:

The effect of 24 mg insulin and/or 16 mg insulin on weighted mean nighttime glucose levels will determined by comparison of weighted mean nighttime glucose levels for insulin-treated groups vs. the group receiving placebo.

The effect of 24 mg insulin and/or 16 mg insulin on changes from baseline to the treatment phase in fasting morning blood glucose, morning fasting serum insulin, morning fasting c-peptide, HbA1c, and triglycerides.

The effect of 24 mg insulin and/or 16 mg insulin on changes from baseline to the treatment phase in mean glucose assessed by CGM.

In still other experiments, recombinant BBI (optionally with KTI and/or aprotinin) is used as described above in place of purified BBI and KTI. In other experiments, synthetic BBI (optionally with KTI and/or aprotinin) is used as described above in place of purified BBI and KTI.

Example 11: Testing of Oral Insulin Formulations Containing Improved SBTI in Treatment of Unstable Diabetes Subjects with unstable diabetes (for example, subject having a glycated hemoglobin [HgA1c] level of 8-10%) are monitored for several days using a blinded continuous glucose monitor (CGM) to establish a baseline. During several subsequent days, they are administered an insulin-containing formulation described herein, optionally using prior art formulations as a control group, prior to meals. Blinded CGM is performed to determine the efficacy of the formulations.

In still other experiments, recombinant BBI (optionally with KTI and/or aprotinin) is used as described above in place of purified BBI and KTI. In other experiments, synthetic BBI (optionally with KTI and/or aprotinin) is used as described above in place of purified BBI and KTI.

Example 12: Testing of Oral Insulin Formulations Containing Improved BBI in the Absence of Other Protease Inhibitors Additional studies are performed, similar to those described above, but using BBI prepared as described herein, in the absence of KTI (e.g. BBI and aprotinin as the only protease inhibitors), and in other experiments, in the absence of any other protease inhibitors. The ability of the improved BBI alone to protect protein drugs in the described formulations in the absence of other protease inhibitors confirms the superiority of BBI prepared as described herein.

In the claims, the word "comprise", and variations thereof such as "comprises", "comprising", and the like indicate that the components listed are included, but not generally to the exclusion of other components.

REFERENCES

Eldor R, Kidron M, Arbit E. Open-label study to assess the safety and pharmacodynamics of five oral insulin formulations in healthy subjects. *Diabetes Obes Metab.* March 2010A; 12(3):219-223.

Eldor R, Kidron M, Greenberg-Shushlav Y, Arbit E. Novel glucagon-like peptide-1 analog delivered orally reduces postprandial glucose excursions in porcine and canine models. *J Diabetes Sci Technol.* 2010B; 4(6):1516-1523.

Kessler L, Passemard R, Oberholzer J et al: Reduction of blood glucose variability in type 1 diabetic patients treated by pancreatic islet transplantation. Diabetes Care 25:2256-2262, 2002.

Kidron M, Dinh S, Menachem Y, et al. A novel per-oral insulin formulation: proof of concept study in non-diabetic subjects. *Diabet Med.* April 2004; 21(4):354-357.

Nissan A, Ziv E, Kidron M, et al. Intestinal absorption of low molecular weight heparin in animals and human subjects. *Haemostasis.* September-October 2000; 30(5): 225-232.

Ryan E A, Shandro T, Green K et al. Assessment of the severity of hypoglycemia and glycemic lability in type 1 diabetic subjects undergoing islet transplantation. *Diabetes.* 2004 April; 53(4):955-62.

Schlichtkrull J, Munck O, Jersild M: The M-value, an index of blood-sugar control in diabetics. *Acta Med Scand.* 177:95-102, 1965.

Service F J, Molnar G D, Rosevear J W et al. Mean amplitude of glycemic excursions, a measure of diabetic instability. *Diabetes.* 1970 September; 19(9):644-55.

Siepmann F, Siepmann J et al, Blends of aqueous polymer dispersions used for pellet coating: importance of the particle size. *J Control Release.* 2005; 105(3): 226-39.

Sprecher C A, Morgenstern K A, Mathewes S, Dahlen J R, Schrader S K, Foster D C, Kisiel W. *J Biol Chem.* 1995 Dec. 15; 270(50):29854-61.

Sun J., Rose J. B., Bird P. (1995) *J. Biol. Chem.* 270, 16089-16096.

Ziv E, Kidron M, Raz I, et al. Oral administration of insulin in solid form to nondiabetic and diabetic dogs. *J Pharm Sci.* June 1994; 83(6):792-794.

The invention claimed is:

1. An oral pharmaceutical composition produced by a process comprising
   (a) subjecting soybean trypsin inhibitor (SBTI) to column chromatography under conditions in which fractions containing the SBTI's Bowman-Birk Inhibitor (BBI) activity elute separately from fractions containing the SBTI's Kunitz Trypsin Inhibitor (KTI) activity;
   (b) eluting and combining fractions from (a) that contain the BBI activity;
   (c) filtering the combined fractions from (b) that contain the BBI activity under conditions that reduce the contaminants having a molecular weight of greater than 30 KDa to be less than 0.1% of the BBI preparation, thus producing a purified BBI product characterized in that:
      (i) contaminants having a molecular weight greater than 30 KDa are less than 0.1% of the preparation; and
      (ii) 1 mg of the purified BBI product has an activity of about 40 BTEE units per mg of protein;
   (d) eluting and combining the fractions from (a) that contain the KTI activity and in which contaminants having a molecular weight greater than 30 KDa are less than 0.1% of the preparation thus producing a purified KTI product characterized in that:
      (i) contaminants having a molecular weight greater than 30 KDa are less than 0.1% of the preparation; and
      (ii) 1 mg of the purified KTI product has an activity of about 10,000 BASE units per mg of protein;
   (e) combining
      (i) an oil-based liquid formulation, wherein the oil comprises fish oil,
      (ii) a therapeutic protein having a molecular weight of up to 100 kilodalton,
      (iii) a chelator of divalent cations,
      (iv) the purified BBI product of part (c); and
      (v) the purified KTI product of part (d), such that the ratio of anti-chymotrypsin activity to anti-trypsin activity present in the pharmaceutical composition is between 1.5:1 and 1:1 inclusive.

2. The oral pharmaceutical composition of claim 1, wherein the composition comprises a coating that resists degradation in the stomach.

3. The oral pharmaceutical composition of claim 2, wherein the coating is a pH-sensitive capsule or a soft gel capsule.

4. The oral pharmaceutical composition of claim 1, wherein the composition is water-free.

5. The oral pharmaceutical composition of claim 4, wherein the composition comprises a coating that resists degradation in the stomach.

6. The oral pharmaceutical composition of claim 5, wherein the coating is a pH-sensitive capsule or a soft gel capsule.

7. The oral pharmaceutical composition of claim 4, wherein the therapeutic protein is insulin.

8. The oral pharmaceutical composition of claim 4, wherein the therapeutic protein is a GLP-1 analogue.

9. An oral pharmaceutical composition comprising an oil-based liquid formulation, wherein said oil-based liquid formulation comprises fish oil, a therapeutic protein of up to 100 kilodalton, a chelator of divalent cations, and a Bowman-Birk Inhibitor (BBI), wherein the BBI has a ratio of anti-chymotrypsin activity to anti-trypsin activity present of between 1.5:1 and 1:1 inclusive, and wherein the BBI has been produced by a process comprising:
   (a) subjecting soybean trypsin inhibitor (SBTI) to column chromatography under conditions in which fractions containing the SBTI's Bowman-Birk Inhibitor (BBI) activity elute separately from fractions containing the SBTI's Kunitz Trypsin Inhibitor (KTI) activity;
   (b) eluting and combining the fractions from (a) that contain the BBI activity; and
   (c) filtering the combined fractions from (b) that contain the BBI activity under conditions that reduce contaminants having a molecular weight of greater than 30 KDa to be less than 0.1% of the BBI preparation, thus producing a purified BBI product characterized in that:
      (i) contaminants having a molecular weight greater than 30 KDa are less than 0.1% of the preparation; and
      (ii) 1 mg of the purified BBI product has an activity of about 40 BTEE units per mg of protein.

10. The oral composition of claim 9, wherein the composition comprises a coating that resists degradation in the stomach.

11. The oral composition of claim 10, wherein the coating is a pH-sensitive capsule or a soft gel capsule.

12. The oral composition of claim 9, wherein the composition is water-free.

13. The oral composition of claim 12, wherein the composition comprises a coating that resists degradation in the stomach.

14. The oral composition of claim 13, wherein the coating is a pH-sensitive capsule or a soft gel capsule.

15. The oral composition of claim 9, wherein the therapeutic protein is insulin.

16. The oral composition of claim 9, wherein the therapeutic protein is a GLP-1 analogue.

17. An oral pharmaceutical composition produced by a process comprising
 (a) subjecting soybean trypsin inhibitor (SBTI) to column chromatography under conditions in which fractions containing the SBTI's Bowman-Birk Inhibitor (BBI) activity elute separately from fractions containing the SBTI's Kunitz Trypsin Inhibitor (KTI) activity;
 (b) eluting and combining fractions from (a) that contain the BBI activity;
 (c) filtering the combined fractions from (b) that contain the BBI activity under conditions that reduce the contaminants having a molecular weight of greater than 30 KDa to be less than 0.1% of the BBI preparation, thus producing a purified BBI product characterized in that:
   (i) contaminants having a molecular weight greater than 30 KDa are less than 0.1% of the preparation; and
   (ii) 1 mg of the purified BBI product has an activity of about 40 BTEE units per mg of protein;
 (d) eluting and combining the fractions from (a) that contain the KTI activity and in which contaminants having a molecular weight greater than 30 KDa are less than 0.1% of the preparation thus producing a purified KTI product characterized in that:
   (i) contaminants having a molecular weight greater than 30 KDa are less than 0.1% of the preparation; and
   (ii) 1 mg of the purified KTI product has an activity of about 10,000 BASE units per mg of protein;
 (e) combining
   (i) an oil-based liquid formulation,
   (ii) a therapeutic protein having a molecular weight of up to 100 kilodalton,
   (iii) a chelator of divalent cations,
   (iv) the purified BBI product of part (c); and
   (v) the purified KTI product of part (d),
 such that the ratio of anti-chymotrypsin activity to anti-trypsin activity present in the pharmaceutical composition is between 1.5:1 and 1:1 inclusive,
 wherein the composition is water-free and comprises a coating that resists degradation in the stomach.

18. The oral pharmaceutical composition of claim 17, wherein the oil is fish oil.

19. The oral pharmaceutical composition of claim 17, wherein the coating is a pH-sensitive capsule or a soft gel capsule.

20. The oral pharmaceutical composition of claim 17, wherein the therapeutic protein is insulin.

21. The oral pharmaceutical composition of claim 17, wherein the therapeutic protein is a GLP-1 analogue.

22. An oral pharmaceutical composition comprising an oil-based liquid formulation, wherein said oil-based liquid formulation comprises a therapeutic protein of up to 100 kilodalton, a chelator of divalent cations, and a Bowman-Birk Inhibitor (BBI), wherein the composition is water-free and comprises a coating that resists degradation in the stomach, wherein the BBI has a ratio of anti-chymotrypsin activity to anti-trypsin activity present of between 1.5:1 and 1:1 inclusive, and wherein the BBI has been produced by a process comprising:
 (a) subjecting soybean trypsin inhibitor (SBTI) to column chromatography under conditions in which fractions containing the SBTI's Bowman-Birk Inhibitor (BBI) activity elute separately from fractions containing the SBTI's Kunitz Trypsin Inhibitor (KTI) activity;
 (b) eluting and combining the fractions from (a) that contain the BBI activity; and
 (c) filtering the combined fractions from (b) that contain the BBI activity under conditions that reduce contaminants having a molecular weight of greater than 30 KDa to be less than 0.1% of the BBI preparation, thus producing a purified BBI product characterized in that:
   (i) contaminants having a molecular weight greater than 30 KDa are less than 0.1% of the preparation; and
   (ii) 1 mg of the purified BBI product has an activity of about 40 BTEE units per mg of protein.

23. The oral pharmaceutical composition of claim 22, wherein the oil is fish oil.

24. The oral pharmaceutical composition of claim 22, wherein the coating is a pH-sensitive capsule or a soft gel capsule.

25. The oral pharmaceutical composition of claim 22, wherein the therapeutic protein is insulin.

26. The oral pharmaceutical composition of claim 22, wherein the therapeutic protein is a GLP-1 analogue.

* * * * *